United States Patent [19]

Gotou et al.

[11] Patent Number: 5,230,893
[45] Date of Patent: Jul. 27, 1993

[54] STABLE AGROCHEMICAL COMPOSITIONS INCLUDING ALPHA-UNSATURATED AMINE DERIVATIVE AND ACID INCORPORATED INTO A CARRIER

[75] Inventors: Yukio Gotou; Masatoshi Sawamura, both of Tsukuba; Tetsuo Okauchi, Osaka, all of Japan

[73] Assignee: Takeda Chemical Industries, Ltd., Osaka, Japan

[21] Appl. No.: 811,651

[22] Filed: Dec. 23, 1991

[30] Foreign Application Priority Data

Dec. 28, 1990 [JP] Japan ................... 2-409322

[51] Int. Cl.$^5$ .................. A01N 25/14; A01N 43/40
[52] U.S. Cl. .................... 424/409; 424/408
[58] Field of Search ............ 424/405, 408, 409, 489; 514/357, 277

[56] References Cited

U.S. PATENT DOCUMENTS 4,133,878  1/1979  Gough ................ 424/255

FOREIGN PATENT DOCUMENTS 1094952  2/1981  Canada .
 281911  9/1988  European Pat. Off. .
0302389  2/1989  European Pat. Off. .
0302833  8/1989  European Pat. Off. .
0375907  7/1990  European Pat. Off. .
0383091  8/1990  European Pat. Off. .
2228003  8/1990  United Kingdom .

OTHER PUBLICATIONS

Jnl. Agric. Food Chem. 1991, 39, pp. 1320–1325, Rozen et al., "Photostabilization of Tetrahydro-1-nitromethylene)-2H-1,3-thiaziadsorbedon Clays".
Chemical Abstracts, vol. III, No. 19, Nov. 6, 1989, Abstract No. 169376Y.
European Search Report.

Primary Examiner—Thurman K. Page
Assistant Examiner—Neil Levy
Attorney, Agent, or Firm—Wegner, Cantor, Mueller & Player

[57] ABSTRACT

Stable agrochemical compositions are provided by incorporating at least one of the α-unsaturated amine derivatives having the following formula:

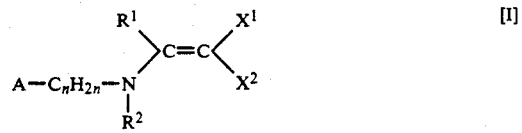

wherein one of $X^1$ and $X^2$ is an electron attracting group and the other is hydrogen or an electron attracting group; $R^1$ is a group attached through a nitrogen atom; $R^2$ is hydrogen or a group attached through a carbon, nitrogen, or oxygen atom; n is an integer of 0, 1, or 2; and A is a substituted or unsubstituted heterocyclic group or a substituted or unsubstituted cyclic hydrocarbon group; and salts thereof, into an agrochemically acceptable solid carrier (clay minerals capable of adsorption (including fuller's earth, terra alba, bentonite, and activated fuller's earth), zeolite, activated charcoal, and β-cyclodextrin, etc.) under a pH 5.5 or less condition. The agrochemical (pesticidal) compositions exert potent shelf life and light-resistance.

10 Claims, No Drawings

STABLE AGROCHEMICAL COMPOSITIONS INCLUDING ALPHA-UNSATURATED AMINE DERIVATIVE AND ACID INCORPORATED INTO A CARRIER

FIELD OF THE INVENTION

The present invention relates to stable agrochemical compositions comprising an α-unsaturated amine derivative or a salt thereof. The compositions of the present invention are useful as pesticidal agents for controlling pests and worms in the agricultural field. The present invention also relates to unique processes for preparing or formulating said agrochemical compositions comprising the α-unsaturated amine derivative or its salt. The processes are useful for stabilizing the α-unsaturated amine derivative or its salt in agrochemical formulations.

BACKGROUND OF THE INVENTION

α-Unsaturated amine derivatives or salts thereof having potent inhibitory actions against harmful pests and the like have been employed as insecticides. It has been found that such amines can be admixed with other insecticides and/or fungicides to form advantageously valuable agrochemical compositions (EPC Patent Application Laid Open No. 302,389; corresponding to Japanese Patent Application Laid Open No. 171/1990).

Further, these compounds are of low toxicity to human beings, domestic animals, fish and natural enemies of pests. For practical use, these compounds are admixed with, for example, a carrier and/or bulking agent to form a conventional solid formulation or preparation such as a dust, granule, wettable powder, wettable granule, seed treating agent, microgranule F, etc.

However, the α-unsaturated amine derivatives and their salts are considerably unstable in the solid formulation wherein said amines are admixed with a carrier and/or bulking agent (e.g. mineral powder). As these compounds are stored at an ambient temperature (30° C.) for long time, they are gradually decomposed. As a result, this causes the formulation to suffer a decrease in the content of the active ingredient. Moreover, in the case where the amine is admixed with one or more species of other agrochemical active substances in order to achieve high activity in a wide range and simultaneous control for saving labor, the decomposition and deterioration of such amines and their salts in the mixed formulation is frequently more serious than that in the single formulation.

The α-unsaturated amine derivatives and their salts have an advantageous property for the environment because of their relatively rapid photodegradation. However, there is a possibility that the preparation could decrease high pesticidal activity by the decomposition of said amines due to sunlight in the case of sprinkling on paddy fields, or uplands.

In general, various techniques for stabilizing agrochemicals have been developed (EPC Patent Application Laid Open No. 280,289; corresponding to Japanese Patent Application Laid Open No. 4/1989 and Japanese Patent Application Laid Open No. 4209/1987). Nevertheless, such prior art techniques cannot solve the problems as described above.

It is still desired to develop a stable agrochemical formulation comprising the α-unsaturated amine derivative or its salt.

SUMMARY OF THE INVENTION

Thus, it is the object of the present invention to provide improved agrochemical compositions which have potent stability and excellent prolonged preventive activity against pests. Further objects of the present invention are to provide agrochemical compositions comprising an α-unsaturated amine derivative or a salt thereof together with at least one of other agrochemically active substances.

The present invention provides novel agrochemical compositions which comprise (i) at least one α-unsaturated amine derivative having the following formula:

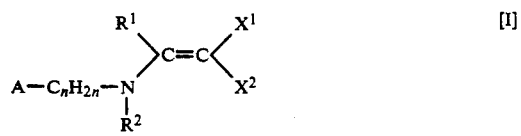

[I]

wherein one of $X^1$ and $X^2$ is an electron attracting group and the other is hydrogen or an electron attracting group; $R^1$ is a group attached through a nitrogen atom; $R^2$ is hydrogen or a group attached through a carbon, nitrogen, or oxygen atom; n is an integer of 0, 1, or 2; and A is a substituted or unsubstituted heterocyclic group or a substituted or unsubstituted cyclic hydrocarbon group; and an agrochemically acceptable salt thereof, and (ii) an acid with an agrochemically acceptable solid carrier, and preparations thereof.

The present invention is based on the observation that agrochemically active substances are stabilized advantageously in agrochemical compositions containing at least an acid and an agrochemically acceptable solid carrier.

The present invention preferably provides novel agrochemical compositions which comprise (i) at least one α-unsaturated amine derivative having the following formula:

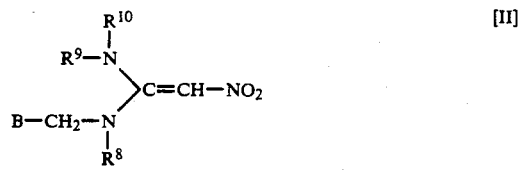

[II]

wherein B is a substituted or unsubstituted 5- or 6-membered heterocyclic group; and $R^8$, $R^9$ and $R^{10}$ are each independently hydrogen or a substituted or unsubstituted hydrocarbon group; and an agrochemically acceptable salt thereof, and (ii) an acid with an agrochemically acceptable solid carrier, and preparations thereof.

DETAILED DESCRIPTION OF THE INVENTION

The present invention relates to an agrochemical composition comprising at least one α-unsaturated amine derivative of the formula [I] or its salt, which exerts improved stability. The composition according to the present invention may contain one or more other agrochemically active substances in addition to the compound [I].

The present invention also relates to a method for preparing or formulating a stable agrochemical composition comprising at least one α-unsaturated amine derivative of the formula [I] or its salt, optionally in admixture with one or more other agrochemically active substances.

The present invention relates importantly to an agrochemical composition comprising at least one α-unsaturated amine derivative of the formula [II] or its salt, which exerts improved stability. The composition according to the present invention may contain one or more other agrochemically active substances in addition to the compound [II].

In the foregoing formula [I], one of $X^1$ and $X^2$ represents an electron attracting group and the other represents hydrogen or an electron attracting group. Examples of the electron attracting group for $X^1$ and $X^2$ include cyano; nitro; alkoxycarbonyl (e.g. $C_{1-4}$ alkoxycarbonyl such as methoxycarbonyl and ethoxycarbonyl); hydoxycarbonyl; $C_{8-10}$ aryloxycarbonyl groups such as phenyloxycarbonyl; heterocyclyloxycarbonyl groups such as pyridyloxycarbonyl and thienyloxycarbonyl (wherein the heterocyclic group includes those mentioned hereinafter); $C_{1-4}$ alkylsulfonyl groups optionally substituted with 1 to 3 halogens, etc. such as methylsulfonyl, trifluoromethylsulfonyl, and ethylsulfonyl; aminosulfonyl; di-$C_{1-4}$ alkoxyphosphoryl such as diethoxyphosphoryl; $C_{1-4}$ acyl groups including alkanoyl optionally substituted with halogen, etc. such as acetyl, trichloroacetyl and trifluoroacetyl; carbamoyl; $C_{1-4}$ alkylsulfonylthiocarbamoyl such as methylsulfonylthiocarbamoyl; and the like.

One of $X^1$ and $X^2$ may include halogens such as fluorine, chlorine, bromine and iodine. $X^1$ and $X^2$ may also be taken together with the nitrogen to which they are attached to form a ring such as

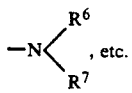

Preferred examples of the group represented by the formula:

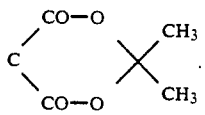

include $O_2N-CH=$, etc.

In the foregoing formula [I], $R^1$ represents a group attached through a nitrogen atom, including a group represented by the formula:

wherein $R^6$ is hydrogen; alkyl (e.g. $C_{1-6}$ alkyl such as methyl, ethyl, n-propyl, i-propyl, n-butyl, i-butyl, and n-hexyl, etc.); $C_{6-10}$ aryl such as phenyl, naphthyl and lower alkyl naphthyl; aralkyl (e.g. $C_{7-9}$ aralkyl such as benzyl, naphthylmethyl, etc.); a heterocyclic group including those mentioned hereinafter (e.g. pyridyl, etc.); $C_{1-4}$ acyl including alkanoyl such as formyl, acetyl and propionyl; $C_{6-10}$ arylcarbonyl such as benzoyl; alkoxycarbonyl (e.g. $C_{1-4}$ alkoxycarbonyl such as methoxycarbonyl and ethoxycarbonyl); $C_{8-10}$ aryloxycarbonyl such as phenyloxycarbonyl; heterocyclyloxycarbonyl such as furyloxycarbonyl (wherein the heterocyclic group includes those mentioned hereinafter); $C_{6-10}$ arylsulfonyl such as phenylsulfonyl; alkylsulfonyl (e.g. $C_{1-4}$ alkylsulfonyl such as methylsulfonyl); dialkoxyphosphoryl (e.g. di-$C_{1-4}$ alkoxyphosphoryl such as diethoxyphosphoryl); alkoxy (e.g. $C_{1-4}$ alkoxy such as methoxy, and ethoxy); hydroxyl; amino; dialkylamino (e.g. di-$C_{1-4}$ alkylamino such as dimethylamino, and diethylamino); acylamino (e.g. $C_{1-4}$ acylamino such as formylamino, acetylamino, and propionylamino); alkoxycarbonylamino (e.g. $C_{1-4}$ alkoxycarbonylamino such as methoxycarbonylamino); alkylsulfonylamino (e.g. $C_{1-4}$ alkylsulfonylamino such as methylsulfonylamino); dialkoxyphosphorylamino (e.g. di-$C_{1-4}$ alkoxyphosphorylamino such as diethoxyphosphorylamino); aralkyloxy (e.g. $C_{7-9}$ aralkyloxy such as benzyloxy and other phenylalkoxy); alkoxycarbonylalkyl (e.g. $C_{1-4}$ alkoxycarbonyl-$C_{1-4}$ alkyl such as methoxycarbonylmethyl); etc. and $R^7$ is hydrogen; alkyl (e.g. $C_{1-4}$ alkyl such as methyl and ethyl); cycloalkyl (e.g. $C_{3-6}$ cycloalkyl such as cyclohexyl); alkenyl (e.g. $C_{2-4}$ alkenyl such as vinyl and allyl); cycloalkenyl (e.g. $C_{3-6}$ cycloalkenyl such as cyclohexenyl); alkynyl (e.g. $C_{2-4}$ alkynyl such as ethynyl); etc. wherein the alkyl, the cycloalkyl, the cycloalkenyl, and the alkynyl may further have 1 to 3 substituents selected from hydroxy, $C_{1-4}$ alkoxy such as methoxy and ethoxy, di-alkylamino such as dimethylamino, $C_{1-4}$ alkylthio such as isopropylthio and n-propylthio, $C_{1-3}$ acylamino such as acetylamino, $C_{1-4}$ alkylsulfonylamino such as methylsulfonylamino, tri-$C_{1-4}$ alkylsilyl such as trimethylsilyl, pyridyl or thiazolyl which may be substituted with 1 to 3 halogens, or $R^6$ and $R^7$, taken together with the nitrogen to which they are attached, may form a 5 or 6-membered cyclic amino group such as

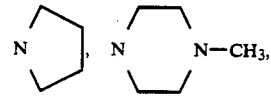

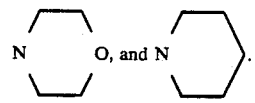

Preferred examples of the group attached through a nitrogen atom for $R^1$ include an amino group optionally substituted with alkyl, aryl, aralkyl, a heterocyclyl, acyl, alkoxycarbonyl, aryloxycarbonyl, heterocyclyloxycarbonyl, arylsulfonyl, alkylsulfonyl, dialkoxyphosphoryl, cycloalkyl, alkenyl, cycloalkenyl, alkynyl, or the like as described herein for $R^6$ and $R^7$ (e.g. disubstituted amino such as di-$C_{1-6}$alkylamino and N-$C_{1-6}$alkyl-N-formylamino; monosubstituted amino such as mono-$C_{1-6}$ alkylamino; and unsubstituted amino); a hydrazino group optionally substituted with alkyl, acyl, alkoxycarbonyl, alkylsulfonyl, dialkoxyphosphoryl, or the like as described hereinafter for $R^3$; a hydroxyamino group optionally substituted with alkyl, aralkyl, or the like as described hereinafter for $R^3$.

Specifically, preferred examples of the group for $R^1$ is the group represented by the formula:

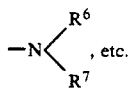

wherein

R$^6$ and R$^7$ have the same meanings as defined above.

R$^2$ represents hydrogen or a group attached through a carbon, nitrogen, or oxygen atom.

Examples of the group attached through a carbon atom for R$^2$ include C$_{1-3}$ acyl (including alkanoyl) such as formyl, acetyl and propionyl; alkyl (e.g. C$_{1-4}$ alkyl such as methyl, ethyl, n-propyl, i-propyl, n-butyl, i-butyl, sec-butyl, etc.); alkenyl (e.g. C$_{2-4}$ alkenyl such as vinyl and allyl); cycloalkyl (e.g. C$_{3-6}$ cycloalkyl such as cyclopentyl and cyclohexyl); C$_{6-10}$ aryl such as phenyl, etc.; aralkyl (e.g. C$_{7-9}$ aralkyl such as benzyl, etc.); a heterocyclic group attached through a carbon atom, including those mentioned hereinafter (e.g. 3- or 4-pyridyl, etc.); and the like. These groups may have 1 to 3 substituent groups which are the same or different. Examples of such substituent groups include C$_{1-4}$ alkylthio such as methylthio, and ethylthio; C$_{1-4}$ alkoxy such as methoxy, and ethoxy; mono- or di-C$_{1-4}$ alkylamino such as methylamino, and dimethylamino; C$_{1-4}$ alkoxycarbonyl such as methoxycarbonyl and ethoxycarbonyl; C$_{1-4}$ alkylsulfonyl such as methylsulfonyl and ethylsulfonyl; halogen such as fluorine, chlorine, bromine and iodine; C$_{1-4}$ acyl (including alkanoyl) such as acetyl; benzoyl; phenylsulfonyl; pyridyl; etc.

Examples of the group attached through a nitrogen atom for R$^2$ include those mentioned for R$^1$.

Examples of the group attached through an oxygen atom for R$^2$ include alkoxy (e.g. C$_{1-4}$ alkoxy such as methoxy, and ethoxy); cycloalkyloxy (e.g. C$_{3-6}$ cycloalkyloxy such as cyclohexyloxy); alkenyloxy (e.g. C$_{2-4}$ alkenyloxy such as vinyloxy and allyloxy); cycloalkenyloxy (e.g. C$_{3-6}$ cycloalkenyloxy such as cyclohexenyloxy); alkynyloxy (e.g. C$_{2-4}$ alkynyloxy such as ethynyloxy); C$_{6-10}$ aryloxy such as phenyloxy and naphthyloxy; heterocyclyloxy wherein the heterocyclic group includes those mentioned hereinafter (e.g. thienyloxy, etc.); and hydroxyl. These groups may have 1 to 3 substituent groups which are the same or different. Examples of such substituent groups include halogen such as fluorine, chlorine, and bromine; phenyl; etc.

Preferred examples of the group for R$^2$ are groups attached through a carbon, nitrogen, or oxygen atom, including formyl; alkyl (e.g. C$_{1-4}$ alkyl such as methyl and ethyl) optionally substituted with C$_{1-4}$ alkylthio, C$_{1-4}$ alkoxy, mono- or di-C$_{1-4}$ alkylamino, C$_{1-4}$ alkoxycarbonyl, C$_{1-4}$ alkylsulfonyl, halogen such as fluorine and chlorine, acetyl, benzoyl, phenylsulfonyl, pyridyl, or the like as mentioned above; optionally substituted amino (e.g. the optionally substituted amino as mentioned for R$^1$); hydroxyl optionally substituted with C$_{1-4}$ alkyl, C$_{3-6}$ cycloalkyl, C$_{2-4}$ alkenyl, C$_{3-6}$ cycloalkenyl, C$_{2-4}$ alkynyl, C$_{6-10}$ aryl, heterocyclyl or the like (e.g. C$_{1-4}$ alkoxy such as methoxy, and ethoxy); and the like.

n is 0, 1 or 2.

The group —C$_n$H$_{2n}$— in the formula [1] represents a single bond, —CH$_2$—, —CH$_2$CH$_2$—, or

preferably a single bond or —CH$_2$—.

A represents a heterocyclic group (e.g. a heterocyclic group optionally substituted with 1 to three substituents as described hereinbelow, especially the substituent (i), (iv), (viii), (xvii), (xLvi), or (xLviii)).

Examples of A include 3-pyridyl, 6-chloro-3-pyridyl, 6-methoxy-3-pyridyl, 6-methyl-3-pyridyl, 6-bromo-3-pyridyl, 6-fluoro-3-pyridyl, 2-chloro-5-thiazolyl, 4-pyridyl, 2-pyrazinyl, 2-thiazolyl, 4-thiazolyl, 3-quinolyl, and the like.

A also represents a cyclic hydrocarbon group (e.g. a cyclic hydrocarbon group optionally substituted with 1 or two substituents as described hereinafter, especially the substituent (xvii)).

Examples of such groups include C$_{3-6}$ cycloalkyl such as cyclopropyl, cyclohexyl, and phenyl, p-chlorophenyl, and the like.

Preferred examples of the heterocyclic group for A are optionally substituted pyridyl or thiazolyl such as 3-pyridyl, 4-pyridyl, 6-chloro-3-pyridyl, 6-bromo-3-pyridyl, 6-fluoro-3-pyridyl, and 2-chloro-5-thiazolyl.

Preferred examples of the cyclic hydrocarbon group for A are halogenophenyl such as p-chlorophenyl.

The alkyl, cycloalkyl, alkenyl, cycloalkenyl, alkynyl, aryl, aralkyl, heterocyclyl, and cyclic hydrocarbon groups for X$^1$, X$^2$, R$^1$, R$^2$, R$^6$, R$^7$ and A include those mentioned below, optionally substituted with 1 to 5 substituents such as (i) to (Lii) listed below.

The alkyl group has preferably 1 to about 20 carbon atoms, more preferably 1 to 8 carbon atoms. The alkyl group may have a straight or branched chain.

Examples of such alkyl groups include methyl, ethyl, propyl, isopropyl, butyl, isobutyl, sec-butyl, pentyl, hexyl, heptyl, octyl, nonyl, 2-ethylhexyl, decyl, undecyl, dodecyl, tridecyl, tetradecyl, pentadecyl, hexadecyl, octadecyl, nonadecyl, eicocyl, and the like.

The cycloalkyl group has preferably 3 to about 6 carbon atoms, and includes, for example, cyclopropyl, cyclobutyl, cyclopentyl, cyclohexyl, and the like.

The alkenyl group, which may be straight or branched, has preferably 2 to about 6 carbon atoms, and includes, for example, vinyl, allyl, isopropenyl, methacryl, 1,1-dimethylallyl, 2-butenyl, 2-pentenyl, 4-pentenyl, 5-hexenyl, and the like.

The cycloalkenyl group, which may be branched, has preferably 3 to about 6 carbon atoms, and includes, for example, 1-cyclopropenyl, 2-cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl, 1,3-cyclohexadien-1-yl, 1,4-cyclohexadien-1-yl, 1,3-cyclopentadien-1-yl, 2,4-cyclopentadien-1-yl, and the like.

The alkynyl group, which may be straight or branched, has preferably has 2 to about 6 carbon atoms, and includes, for example, ethynyl, propargyl, 2-butyn-1-yl, 3-butyn-1-yl, 3-butyn-2-yl, 1-pentyn-3-yl, 3-pentyn-1-yl, 4-pentyn-2-yl, 3-hexyn-1-yl, and the like.

The aryl group includes, for example, phenyl, naphthyl and the like.

The aralkyl group includes, for example, benzyl, phenethyl, naphthylmethyl and the like.

The heterocyclic group is a cyclic group containing only the same heteroatoms or a cyclic group containing two or more different heteroatoms, e.g. a heterocyclic group having a single or fused ring with 5 to 8 ring members in each ring and having from one to five heteroatoms in each ring independently selected from oxygen, nitrogen and sulfur. Examples of the heterocyclic group include 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl; 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxide of 2-, 3- or 4-pyridyl, 2-, 4- or 5-pyrimidinyl, N-oxide of 2-, 4- or 5-pyrimidinyl, 3- or 4-pyridazinyl, pyrazinyl, N-oxide of 3- or 4-pyridazinyl, benzofuryl, benzothiazolyl, benzoxazolyl, triazinyl, oxotriazinyl, tetrazolo[1,5-b]pyridazinyl, triazolo[4,5-b]pyridazinyl, oxoimidazolyl, dioxotriazinyl, pyrrolidinyl, piperidyl, pyranyl, thiopyranyl, 1,4-oxazinyl, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl, and phenoxazinyl.

The cyclic hydrocarbon group includes, for example, $C_{3-6}$ cycloalkyl such as cyclopropyl, cyclobutyl, cyclopentyl, and cyclohexyl, $C_{3-6}$ cycloalkenyl such as 1-cyclopropenyl, 2-cyclobutenyl, 1-cyclohexenyl, 2-cyclohexenyl, and cyclopentyloxy, cyclohexyloxy, etc. 1,3-cyclohexadien-1-yl, and $C_{6-10}$ aryl such as phenyl, and naphthyl.

(i) $C_{1-4}$ Alkyl groups include, for example, methyl, ethyl, propyl, isopropyl, butyl, isobutyl, sec-butyl, tert-butyl, etc.

(ii) $C_{3-6}$ Cycloalkyl groups include, for example, cyclopropyl, cyclobutyl, cyclopentyl, cyclohexyl, etc.

(iii) $C_{6-10}$ Aryl groups include, for example, phenyl, naphthyl, etc.

(iv) $C_{1-4}$ Alkoxy groups include, for example, methoxy, ethoxy, propoxy, isopropoxy, butoxy, tert-butoxy, etc.

(v) $C_{3-6}$ Cycloalkoxy groups include, for example, cyclopropyloxy, (vi) $C_{6-10}$ Aryloxy groups include, for example, phenoxy, naphthyloxy, etc.

(vii) $C_{7-12}$ Aralkyloxy groups include, for example, benzyloxy, 2-phenethyloxy, 1-phenethyloxy, etc.

(viii) $C_{1-4}$ Alkylthio groups include, for example, methylthio, ethylthio, propylthio, butylthio, etc.

(ix) $C_{3-6}$ Cycloalkylthio groups include, for example, cyclopropylthio, cyclopentylthio, cyclohexylthio, etc.

(x) $C_{6-10}$ Arylthio groups include, for example, phenylthio, naphthylthio, etc.

(xi) $C_{7-12}$ Aralkylthio groups include, for example, benzylthio, 2-phenethylthio, 1-phenethylthio, etc.

(xii) Mono-$C_{1-4}$ alkylamino groups include, for example, methylamino, ethylamino, propylamino, isopropylamino, butylamino, isobutylamino, tert-butylamino, etc.

(xiii) Di-$C_{1-4}$ alkylamino groups include, for example, dimethylamino, diethylamino, dipropylamino, dibutylamino, N-methyl-N-ethylamino, N-methyl-N-propylamino, N-methyl-N-butylamino, etc.

(xiv) $C_{3-6}$ Cycloalkylamino groups include, for example, cyclopropylamino, cyclopentylamino, cyclohexylamino, etc.

(xv) $C_{6-10}$ Arylamino groups include, for example, anilino, etc.

(xvi) $C_{7-12}$ Aralkylamino groups include, for example, benzylamino, 2-phenethylamino, 1-phenethylamino, etc.

(xvii) Halogens include, for example, fluorine, chlorine, bromine, iodine, etc.

(xviii) $C_{1-4}$ Alkoxycarbonyl groups include, for example, methoxycarbonyl, ethoxycarbonyl, propoxycarbonyl, isopropoxycarbonyl, butoxycarbonyl, tert-butoxycarbonyl, isobutoxycarbonyl, etc.

(xix) $C_{6-10}$ Aryloxycarbonyl groups include, for example, phenoxycarbonyl, etc.

(xx) $C_{3-6}$ Cycloalkoxycarbonyl groups include, for example, cyclopropyloxycarbonyl, cyclopentyloxycarbonyl, cyclohexyloxycarbonyl, etc.

(xxi) $C_{7-12}$ Aralkyloxycarbonyl groups include, for example, benzyloxycarbonyl, 1-phenethyloxycarbonyl, 2-phenethyloxycarbonyl, etc.

(xxii) $C_{1-5}$ Alkanoyl groups include, for example, formyl, acetyl, propionyl, butyryl, pivaloyl, etc.

(xxiii) $C_{1-15}$ Alkanoyloxy groups include, for example, formyloxy, acetyloxy, butyryloxy, pivaloyloxy, pentanoyloxy, hexanoyloxy, hepanoyloxy, octanoyloxy, nonanoyloxy, decanoyloxy, undecanoyloxy, dodecanoyloxy, tridecanoyloxy, tetradecanoyloxy, pentadecanoyloxy, and the like.

(xxiv) Optionally substituted carbamoyl groups include, for example, carbamoyl, N-methylcarbamoyl, N,N-dimethylcarbamoyl, N-ethylcarbamoyl, N,N-diethylcarbamoyl, N-phenylcarbamoyl, pyrrolidinocarbamoyl, piperidinocarbamoyl, piperazinocarbamoyl, morpholinocarbamoyl, N-benzylcarbamoyl, etc.

(xxv) Optionally substituted carbamoyloxy groups include, for example, N-methylcarbamoyloxy, N,N-dimethylcarbamoyloxy, N-ethylcarbamoyloyx, N-benzylcarbamoyloxy, N,N-dibenzylcarbamoyloxy, N-phenylcarbamoyloxy, etc.

(xxvi) $C_{1-4}$ Alkanoylamino groups include, for example, formylamino, acetamido, propionamido, butyrylamido, etc.

(xxvii) $C_{6-10}$ Arylcarbonylamino groups include, for example, benzamido, etc.

(xxviii) $C_{1-4}$ Alkoxycarbonylamino groups include, for example, methoxycarbonylamino, ethoxycarbonylamino, butoxycarbonylamino, tert-butoxycarbonylamino, etc.

(xxix) $C_{7-12}$ Aralkyloxycarbonylamino groups include, for example, benzyloxycarbonylamino, 4-methoxybenzyloxycarbonylamino, 4-nitrobenzyloxycarbonylamino, 4-chlorobenzyloxycarbonylamino, etc.

(xxx) Substituted sulfonylamino groups include, for example, methanesulfonylamino, ethanesulfonylamino, butanesulfonylamino, benzenesulfonylamino, toluenesulfonylamino, naphthalenesulfonylamino, trifluoromethanesulfonylamino, 2-chloroethanesulfonylamino, 2,2,2-trifluoroethanesulfonylamino, etc.

(xxxi) Heterocyclic groups are cyclic groups each containing 1 to 5 heteroatoms selected from nitrogen, oxygen and sulfur and include, for example, pyrrolidinyl, 2- or 3-pyrrolyl, 3-, 4- or 5-pyrazolyl, 2-, 4- or 5-imidazolyl, 2- or 3-furyl, 2-or 3-thienyl, 2-, 4- or 5-oxazolyl, 3-, 4- or 5-isoxazolyl, 3-, 4-or 5-isothiazolyl, 2-, 4- or 5-thiazolyl, piperidinyl, 2-, 3- or 4-pyridyl, piperazinyl, pyrimidinyl, pyranyl, tetrahydropyranyl, tetrahydrofuryl, indolyl, quinolyl, 1,3,4-oxadiazolyl, thieno[2,3-d]pyridyl, 1,2,3-thiadiazolyl, 1,3,4-thiadiazolyl, 1,2,3-triazolyl, 1,2,4-triazolyl, 1,3,4-triazolyl, tetrazolyl, 4, 5-dihydro-1,3-dioxolyl, tetrazolo[1,5-b]pyridazinyl, benzothiazolyl, benzoxazolyl, benzimidazolyl, benzothienyl, etc.

(xxxii) Heterocyclylthio, heterocyclyloxy, heterocyclylamino, and heterocyclylcarbonylamino groups are heterocyclic groups attached through sulfur, nitrogen, oxygen and carbonyl respectively wherein the heterocyclyl portion is the above-mentioned group (xxxi).

(xxxiii) Di-$C_{1-4}$ alkylphosphinothioylamino groups include, for example, dimethylphosphinothioylamino, diethylphosphinothioylamino, etc.

(xxxiv) Alkoxyimino groups include, for example, methoxyimino, ethoxyimino, 2-fluoroethoxyimino, carboxymethoxyimino, 1-carboxy-1-methylethoxyimino, 2,2,2-trichloroethyloxycarbonylmethoxyimino, 1-(2,2,2-trichloroethyloxycarbonyl)-1-methylethoxyimino, (2-aminothiazol-4-yl)methoxyimino, (1H-imidazol-4-yl)methoxyimino, etc.

(xxxv) $C_{1-4}$ Alkylsulfonyloxy groups include, for example, methanesulfonyloxy, ethanesulfonyloxy, butanesulfonyloxy, etc.

(xxxvi) $C_{6-10}$ Arylsulfonyloxy groups include, for example, benzenesulfonyloxy, toluenesulfonyloxy, etc.

(xxxvii) Di-$C_{6-10}$ arylphosphinothioylamino groups include, for example, diphenylphosphinothioylamino, etc.

(xxxviii) Optionally substituted thiocarbamoylthio groups include, for example, thiocarbamoylthio, N-methylthiocarbamoylthio, N,N-dimethylthiocarbamoylthio, N-ethylthiocarbamoylthio, N-benzylthiocarbamoylthio, N,N-dibenzylthiocarbamoylthio, N-phenylthiocarbamoylthio, etc.

(xxxix) Silyloxy groups include tri-$C_{1-4}$ alkylsilyloxy groups such as trimethylsilyloxy and tert-butyldimethylsilyloxy, mixed $C_{1-4}$ alkyl-phenylsilyloxy groups such as tert-butyldiphenylsilyloxy, and dimethylphenylsilyloxy, etc.

(xL) Silyl groups include tri-$C_{1-4}$ alkylsilyl groups such as trimethylsilyl and tert-butyldimethylsilyl, mixed $C_{1-4}$ alkyl-phenylsilyl groups such as tert-butyldiphenylsilyl, and dimethylphenylsilyl, etc.

(xLi) $C_{1-4}$ Alkylsulfinyl groups include, for example, methylsulfinyl, ethylsulfinyl, propylsulfinyl, butylsulfinyl, etc.

(xLii) $C_{6-10}$ Arylsulfinyl groups include, for example, phenylsulfinyl, naphthylsulfinyl, etc.

(xLiii) $C_{1-4}$ Alkylsulfonyl groups include, for example, methanesulfonyl, ethanesulfonyl, butanesulfonyl, etc.

(xLiv) $C_{6-10}$ Arylsulfonyl groups include, for example, benzenesulfonyl, toluenesulfonyl, etc.

(xLv) $C_{1-4}$ Alkoxycarbonyloxy groups include, for example, methoxycarbonyloxy, ethoxycarbonyloxy, tert-butoxycarbonyloxy, etc.

(xLvi) $C_{1-4}$ Haloalkyl groups include $C_{1-4}$ alkyl groups with 1 to 4 halogen atoms such as trifluoromethyl, 1,1,2,2-tetrafluoroethyl, difluoromethyl, monofluoromethyl, trichloromethyl, dichloromethyl, monochloromethyl, and the like.

(xLvii) $C_{1-4}$ Haloalkyloxy, $C_{1-4}$ haloalkylthio, $C_{1-4}$ haloalkylsulfinyl, and $C_{1-4}$ haloalkylsulfonyl groups are, for example, $C_{1-4}$ haloalkyl groups attached through an oxygen, sulfur and nitrogen atom, a sulfinyl and sulfonyl group, respectively wherein the $C_{1-4}$ haloalkyl portion is the above-mentioned group (xLvi).

(xLviii) Cyano, nitro, hydroxyl, carboxyl, sulfo ($-SO_3H$), and phosphono ($-PO_3H_2$).

(xLix) $C_{1-4}$ Alkyloxysulfonyl groups include, for example, methoxysulfonyl, ethoxysulfonyl, butoxysulfonyl, etc.

(L) $C_{6-10}$ Aryloxysulfonyl groups include, for example, phenoxysulfonyl, tolyloxysulfonyl, etc.

(Li) $C_{7-12}$ Aralkyloxysulfonyl groups include, for example, benzyloxysulfonyl, 2-phenethyloxysulfonyl, 1-phenethyloxysulfonyl, etc.

(Lii) Di-$C_{1-4}$ alkyloxyphosphoryl groups include, for example, dimethoxyphosphoryl, diethoxyphosphoryl, dibutoxyphosphoryl, etc.

Among the compounds represented by the above formula (I), preferred examples of the invention are compounds of the formula:

$$O_2N-CH=\overset{\overset{R^{1a}}{|}}{C}-\overset{\overset{R^{2a}}{|}}{N}-CH_2-A^a \qquad [I^a]$$

wherein $R^{1a}$ is mono-$C_{1-6}$ alkylamino, N-$C_{1-6}$ alkyl-N-formylamino, or amino, $R^{2a}$ is $C_{1-4}$ alkyl or $C_{1-4}$ alkoxy and $A^a$ is chloropyridyl;

$$O_2N-CH=\overset{\overset{R^{1b}}{|}}{C}-NH-CH_2-A^a \qquad [I^b]$$

wherein $R^{1b}$ is mono-$C_{1-6}$ alkylamino, or N-$C_{1-6}$ alkyl-N-formylamino, and $A^a$ is of the same meaning as defined above;

$$O_2N-CH=\overset{\overset{R^{1c}}{|}}{C}-\overset{\overset{R^{2b}}{|}}{N}-CH_2-A^b \qquad [I^c]$$

wherein $R^{1c}$ is di-$C_{1-6}$ alkylamino, $R^{2b}$ is hydrogen, formyl, or $C_{1-4}$ alkyl and $A^b$ is pyridyl or chloropyridyl; or $$\overset{X^1}{\underset{X^2}{>}}C=\overset{\overset{R^1}{|}}{C}-\overset{\overset{R^2}{|}}{N}-A \qquad [I^d]$$

wherein each group is of the same meaning as defined above; or agrochemically acceptable salts thereof.

The mono-$C_{1-6}$ alkylamino groups for $R^{1a}$ and $R^{1b}$ in the formulas [$I^a$], [$I^b$], and [$I^c$] include, for example, monomethylamino, monoethylamino, mono-n-propylamino, mono-i-propylamino, mono-n-butylamino, mono-i-butylamino, mono-n-hexylamino, etc. Preferred examples of such mono-$C_{1-6}$ alkylamino groups are mono-$C_{1-4}$ alkylamino such as monomethylamino, and monoethylamino.

The N-$C_{1-6}$ alkyl-N-formylamino groups for $R^{1a}$ and $R^{1b}$ include, for example, N-methyl-N-formylamino, N-ethyl-N-formylamino, N-n-propyl-N-formylamino, N-i-propyl-N-formylamino, N-n-butyl-N-formylamino, N-n-hexyl-N-formylamino, etc. Preferred examples of such N-$C_{1-6}$ alkyl-N-formylamino groups are N-$C_{1-4}$ alkyl-N-formylamino such as N-methyl-N-formylamino, and N-ethyl-N-formylamino.

The di-$C_{1-6}$ alkylamino groups for $R^{1c}$ include, for example, dimethylamino, N-ethyl-N-methylamino, diethylamino, di-n-propylamino, di-i-propylamino, di-n-butylamino, di-i-butylamino, di-n-pentylamino, di-i-pentylamino, di-n-hexylamino, etc. Preferred examples of such di-$C_{1-6}$ alkylamino groups are di-$C_{1-4}$ alkylamino such as dimethylamino, N-ethyl-N-methylamino, and diethylamino.

The $C_{1-4}$ alkyl groups for $R^{2a}$ and $R^{2c}$ include, for example, those mentioned above for $R^2$. Preferred examples of such $C_{1-4}$ alkyl groups are methyl, ethyl, etc.

The $C_{1-4}$ alkoxy groups for $R^{2a}$ include, for example, those mentioned above for $R^2$. Preferred examples of such $C_{1-4}$ alkoxy groups are methoxy, ethoxy, etc.

The chloropyridyl groups for $A^a$ and $A^b$ include, for example, 2-chloro-3-pyridyl, 4-chloro-3-pyridyl, 5-chloro-3-pyridyl, 6-chloro-3-pyridyl, 3-chloro-4-pyridyl, etc. Preferred examples of such chloropyridyl groups are 6-chloro-3-pyridyl, etc.

The pyridyl groups for $A^b$ include, for example, 3-pyridyl, 4-pyridyl, etc. Preferred examples of such pyridyl groups are 3-pyridyl, etc.

Among the compounds represented by the above formula (I), preferred examples of the invention are compounds of the formula:

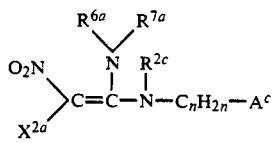  [I$^e$]

wherein $X^{2a}$ is hydrogen, $C_{1-4}$ alkoxycarbonyl or $C_{1-4}$ alkylsulfonylthiocarbamoyl; $R^{2c}$ is hydrogen, $C_{1-3}$ acyl, $C_{1-4}$ alkyl, mono- or di-$C_{1-4}$ alkoxy-$C_{1-4}$ alkyl, $C_{7-8}$ aralkyl, mono- or di-$C_{1-4}$ alkylamino or $C_{1-4}$ alkoxy; $A^c$ is 3- or 4-pyridyl, pyrazinyl, or 4- or 5-thiazolyl, optionally substituted with halogen, $C_{1-4}$ alkyl or $C_{1-4}$ alkoxy; $R^{6a}$ and $R^{7a}$ are each hydrogen, lower alkyl, halogenated lower alkyl, or $C_{1-4}$ acyl; n is of the same meaning as defined above.

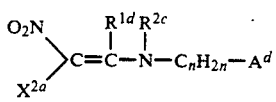  [I$^f$]

wherein $X^{2a}$ is hydrogen, $C_{1-4}$ alkoxycarbonyl or $C_{1-4}$ alkylsulfonylthiocarbamoyl; $R^{1d}$ is amino, mono- or di-$C_{1-4}$ alkylamino, N-$C_{1-4}$ alkyl-N-$C_{1-3}$ acylamino, $C_{7-9}$ aralkylamino, halogenothiazolyl-$C_{1-2}$ alkylamino, or $C_{1-4}$ alkoxy-$C_{1-2}$ alkylamino; $R^{2c}$ is hydrogen, $C_{1-3}$ acyl, $C_{1-4}$ alkyl, mono- or di-$C_{1-4}$ alkoxy-$C_{1-4}$ alkyl, $C_{7-8}$ aralkyl, mono- or di-$C_{1-4}$ alkylamino or $C_{1-4}$ alkoxy; n is 0, 1 or 2; $A^d$ is 3- or 4-pyridyl, pyrazinyl, or 5-thiazolyl, optionally substituted with halogen, $C_{1-4}$ alkyl or $C_{1-4}$ alkoxy;

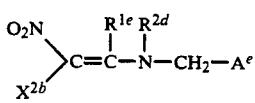  [I$^g$]

wherein $X^{2b}$ is hydrogen, or $C_{1-2}$ alkylsulfonylthiocarbamoyl; $R^{1e}$ is amino, mono- or di-$C_{1-2}$ alkylamino, or N-$C_{1-2}$ alkyl-N-formylamino; $R^{2d}$ is hydrogen, or $C_{1-3}$ acyl; and $A^e$ is a group having the formula:

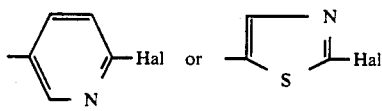

wherein Hal is halogen;

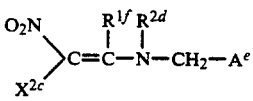  [I$^h$]

wherein $X^{2c}$ is hydrogen, or methylsulfonylthiocarbamoyl; $R^{1f}$ is amino, methylamino, dimethylamino, or N-methyl-N-formylamino; $R^{2d}$ is hydrogen, formyl, or $C_{1-2}$ alkyl; and $A^e$ is a group having the formula:

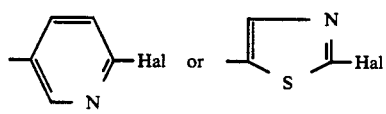

wherein Hal is halogen; or

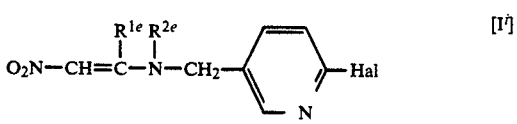  [I$^i$]

wherein $R^{1e}$ is amino, mono- or di-$C_{1-2}$ alkylamino, or N-$C_{1-2}$ alkyl-N-formylamino; $R^{2e}$ is $C_{1-2}$ alkyl, or formyl; and Hal is halogen; or agrochemically acceptable salts thereof.

With regard to the formulas [I$^e$] to [I$^i$], the groups represented by $X^{2a}$, $X^{2b}$, and $X^{2c}$; $R^{1d}$, $R^{1e}$, and $R^{1f}$; $R^{2c}$, $R^{2d}$, and $R^{2e}$; and $A^c$, $A^d$, and $A^e$ are those mentioned herein for $X^2$, $R^1$, $R^2$, A, respectively. The groups represented by $R^{6a}$ and the groups represented by $R^{7a}$ are those mentioned herein for $R^6$ and $R^7$, respectively.

The compounds represented by the formula [I] and their salts can be prepared by processes as disclosed in EPC Patent Application Laid Open No. 302,389 (corresponding to Japanese Patent Application Laid Open No. 171/1990) or processes analogous to the known methods.

In the foregoing formula [II], $R^8$, $R^9$, and $R^{10}$ represents hydrogen; $C_{1-3}$ acyl groups including alkanoyl groups such as formyl, acetyl, and propionyl; alkyl groups, for example, $C_{1-4}$ alkyl groups such as methyl, ethyl, n-propyl, i-propyl, n-butyl, i-butyl, and sec-butyl; alkenyl groups, for example, $C_{2-4}$ alkenyl such as vinyl, and allyl; alkynyl groups, for example, $C_{2-4}$ alkynyl such as ethynyl 1-propynyl, and 2-propynyl; cycloalkyl groups, for example, $C_{3-6}$ cycloalkyl groups such as cyclopentyl and cyclohexyl; or heterocyclic groups bonded through the carbon atom thereon (including those mentioned herein for B), for example, pyridyl groups such as 3- or 4-pyridyl.

These groups for $R^8$, $R^9$, and $R^{10}$ may have 1 to 3 (preferably 1) substituent groups which are the same or different. Examples of such substituent groups include but are not limited to $C_{1-4}$ alkylthio groups such as methylthio, and ethylthio; $C_{1-4}$ alkoxy groups such as methoxy, and ethoxy; mono- or di-$C_{1-4}$ alkylamino groups such as methylamino, ethylamino, and dimethylamino; $C_{2-5}$ alkoxycarbonyl groups such as methoxycarbonyl, and ethoxycarbonyl; $C_{1-4}$ alkylsulfonyl groups such as methylsulfonyl, and ethylsulfonyl; halogens such as fluorine, chlorine, bromine and iodine; $C_{1-4}$ acyl groups including alkanoyl groups such as acetyl; benzoyl; phenylsulfonyl; and pyridyl.

Preferred examples for $R^8$, $R^9$, and $R^{10}$ are hydrogen; $C_{1-3}$ acyl groups including alkanoyl groups such as formyl, acetyl, and propionyl; and alkyl groups, for example, $C_{1-4}$ alkyl groups such as methyl, ethyl, n-propyl, i-propyl, n-butyl, i-butyl, and sec-butyl.

More preferred examples for $R^8$, $R^9$, and $R^{10}$ are hydrogen; $C_{1-3}$ alkanoyl groups such as formyl, acetyl, and propionyl; and $C_{1-4}$ alkyl groups such as methyl, ethyl, n-propyl, i-propyl, n-butyl, i-butyl, and sec-butyl.

In the foregoing formula [II], B represents a substituted or unsubstituted heterocyclic group having a single or fused ring with 5 or 6 ring members in each ring. Specific examples of suitable five- or six-membered heterocyclic groups include pyridyl groups such as 2-, 3- or 4-pyridyl, thiazolyl groups such as 2-, 4- or 5-thiazolyl and pyrazinyl groups.

These heterocyclic groups may have 1 to 5 (preferably 1) substituent groups which are the same or different. Examples of such substituent groups include but are not limited to $C_{1-4}$ alkyl groups such as methyl, ethyl, propyl, isopropyl, butyl, isobutyl, sec-butyl, and tert-butyl; $C_{1-4}$ alkoxy groups such as methoxy, ethoxy, propoxy, isopropoxy, and tert-butoxy; $C_{1-4}$ alkylthio groups such as methylthio, ethylthio, propylthio, and butylthio; halogens such as fluorine, chlorine, bromine and iodine; $C_{1-4}$ haloalkyl groups such as trifluoromethyl, 1,1,2,2-tetrafluoroethyl, difluoromethyl, monofluoromethyl, trichloromethyl, dichloromethyl, and monochloromethyl; $C_{1-4}$ haloalkoxy groups; $C_{1-4}$ haloalkylthio groups; $C_{1-4}$ haloalkylsulfinyl groups; or $C_{1-4}$ haloalkylsulfonyl groups wherein said $C_{1-4}$ haloalkyl group is attached through an oxygen or sulfur atom, or a sulfinyl or sulfonyl group; cyano; nitro; hydroxyl; carboxyl; sulfo ($-SO_3H$); and phosphono ($-PO_3H_2$).

Preferred examples of B are five- or six-membered heterocyclic groups such as pyridyl and thiazolyl which may be substituted with one or two halogens. Specific examples of B are 3-pyridyl, 4-pyridyl, halogenopyridyl such as 6-chloro-3-pyridyl, 6-bromo-3-pyridyl, 6-fluoro-3-pyridyl, and 5-bromo-3-pyridyl, 6-methoxy-3-pyridyl, 6-methyl-3-pyridyl, 2-thiazolyl, 4-thiazolyl, halogenothiazolyl such as 2-chloro-5-thiazolyl and 2-bromo-5-thiazolyl, 2-pyrazinyl.

More preferred examples of B are 3-pyridyl, 4-pyridyl, 6-chloro-3-pyridyl, 6-bromo-3-pyridyl, 6-fluoro-3-pyridyl, 5-bromo-3-pyridyl, 6-methoxy-3-pyridyl, 6-methyl-3-pyridyl, 2-thiazolyl, 4-thiazolyl, 2-chloro-5-thiazolyl, 2-bromo-5-thiazolyl, 2-pyrazinyl.

Among the compounds represented by the above formula [II], a preferred embodiment is a compound of the formula:

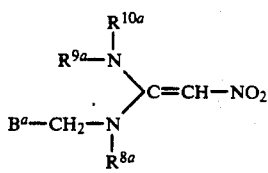

[II$^a$]

wherein $B^a$ is a substituted or unsubstituted pyridyl or thiazolyl group, and $R^{8\,a}$, $R^{9\,a}$, and $R^{10\,a}$ are each independently hydrogen; an alkyl, alkenyl, alkynyl, cycloalkyl, acyl, or alkoxycarbonyl group, or an agrochemically acceptable salt thereof.

In the foregoing formula [II$^a$], a preferred embodiment of $B^a$ is a halogenated group such as a group having the formula:

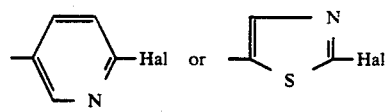

wherein Hal is halogen.

Among the compounds represented by the above formula [II$^a$], a more preferred embodiment is a compound of the formula:

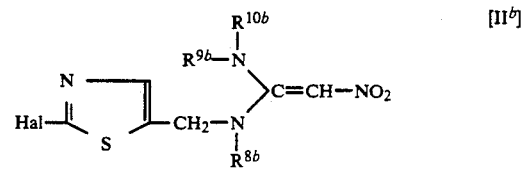

[II$^b$]

wherein $R^{8\,b}$, $R^{9\,b}$, and $R^{10\,b}$ are each independently hydrogen or an alkyl group, and Hal is halogen, or

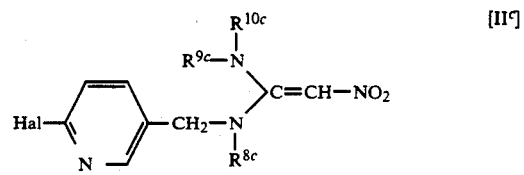

[II$^c$]

wherein $R^{8\,c}$, $R^{9\,c}$, and $R^{10\,c}$ are each independently hydrogen or an alkyl group, and Hal is halogen, or an agrochemically acceptable salt thereof.

The compounds represented by the formula [II] and their salts can be prepared by processes known in the prior arts. The compounds represented by the formula [II] and their salts can also be prepared by processes as disclosed in EPC Patent Application Laid Open No. 302,389 (corresponding to Japanese Patent Application Laid Open No. 171/1990) or processes analogous to the known methods.

In the case where the compound [I] or [II] is obtained in its free form, it can be converted into a corresponding salt by conventional methods. When the compound [I] or [II] is obtained in its salt form, it can be converted into the corresponding free form by conventional methods.

In the case where the compound [I] or [II] has at least one of acidic groups such as carboxyl, sulfo ($-SO_3H$), and phosphono ($-PO_3H_2$), the compound [I] or [II] can form a salt with a base. Examples of such bases include inorganic bases such as sodium, potassium, lithium, calcium, magnesium, and ammonia, and organic bases such as pyridine, collidine, triethylamine, and triethanolamine.

In the case where the compound [I] or [II] has at least one of basic groups such as amino or substituted amino, the compound [I] or [II] can be formed an acid addition salt. Examples of such acid addition salts include salts with inorganic acids such as hydrochloric acid, hydrobromic acid, hydroiodic acid, nitric acid, sulfuric acid, and phosphoric acid, as well as with organic acids such as acetic acid, benzoic acid, maleic acid, fumaric acid, succinic acid, tartaric acid, citric acid, oxalic acid, glyoxalic acid, asparaginic acid, methanesulfonic acid, methanedisulfonic acid, 1,2-ethanedisulfonic acid, and benzenesulfonic acid.

Representative examples of α-unsaturated amine derivatives of the formulas [I] and [II] which can be used in the composition according to the present invention are:

(compound No.1) 1-[N-(6-chloro-3-pyridylmethyl)-N-methyl]amino-1-methylamino-2-nitroethylene;
(compound No.2) 1-(6-chloro-3-pyridylmethyl)amino-1-dimethylamino-2-nitroethylene;
(compound No.3) 1-[N-(6-chloro-3-pyridylmethyl)-N-ethyl]amino-1-methylamino-2-nitroethylene;
(compound No.4) 1-[N-(6-chloro-3-pyridylmethyl)-N-methyl]amino-1-dimethylamino-2-nitroethylene;
(compound No.5) 1-[N-(6-chloro-3-pyridylmethyl)-N-ethyl]amino-1-(N-formyl-N-methyl)amino-2-nitroethylene;
(compound No.6) 1-[N-(2-chloro-5-thiazolylmethyl)-N-ethyl]amino-1-methylamino-2-nitroethylene;
(compound No.7) 1-[N-(2-chloro-5-thiazolylmethyl)-]amino-1-dimethylamino-2-nitroethylene;
(compound No.8) 1-[N-(6-bromo-3-pyridylmethyl)-N-methyl]amino-1-methylamino-2-nitroethylene;
(compound No.9) 1-[N-(6-chloro-3-pyridylmethyl)-N-formyl]amino-1-dimethylamino-2-nitroethylene;
(compound No.10) 1-[N-(6-fluoro-3-pyridylmethyl)-N-methyl]amino-1-methylamino-2-nitroethylene;
(compound No.11) 1-[N-ethyl-N-(6-fluoro-3-pyridylmethyl)]amino-1-methylamino-2-nitroethylene;
(compound No.12) 1-[N-(6-bromo-3-pyridylmethyl)-N-ethyl]amino-1-methylamino-2-nitroethylene;
(compound No.13) 1-[N-(2-chloro-5-thiazolylmethyl)-N-methyl]amino-1-(N-formyl-N-methyl)amino-2-nitroethylene;
(compound No.14) 1-[N-(2-chloro-5-thiazolylmethyl)-N-ethyl]amino-1-(N-formyl-N-methyl)amino-2-nitroethylene;
(compound No.15) 1-[N-(6-bromo-3-pyridylmethyl)-N-methyl]amino-1-(N-formyl-N-methyl)amino-2-nitroethylene;
(compound No.16) 1-[N-(6-bromo-3-pyridylmethyl)-N-ethyl]amino-1-(N-formyl-N-methyl)amino-2-nitroethylene;
(compound No.17) 1-[N-(6-bromo-3-pyridylmethyl)-N-formyl]amino-1-dimethylamino-2-nitroethylene;
(compound No.18) 1-[N-(6-chloro-3-pyridylmethyl)-N-(2,2,2-trifluoroethyl)]amino-1-methylamino-2-nitroethylene;
(compound No.19) 1-[N-(2-chloro-5-thiazolylmethyl)-N-formyl]amino-1-dimethylamino-2-nitroethylene;
(compound No.20) 1-(6-chloro-3-pyridylmethyl)amino-1-methylamino-2-nitroethylene;
(compound No.21) 1-amino-1-[N-(6-chloro-3-pyridylmethyl)-N-methyl]amino-1-methylamino-2-nitroethylene;
and the like.

The α-unsaturated amine derivatives or salts thereof can be employed as insecticide according to the techniques as disclosed in EPC Patent Application Laid Open No. 302,389 (corresponding to Japanese Patent Application Laid Open No. 171/1990).

The present inventors have found that the α-unsaturated amine derivatives or salts thereof can be significantly stabilized during long term storage and against light in agrochemical formulations by employing acids and specific solid carriers.

The present inventors have also found that the α-unsaturated amine derivatives or salts thereof can be incorporated into solid carriers capable of adsorption, among various agrochemical bulking agents, whereby it is possible to improve significantly the long term and light stability of said α-unsaturated amine derivatives or salts thereof in the formulation.

According to one embodiment, the present inventors have succeeded in preparing a pH 5.5 or less aqueous solution (or suspension) of an agrochemically active ingredient (α-unsaturated amine derivative or its salt) and adding said solution (or suspension) to the above-mentioned stabilizer (solid carrier capable of adsorption) to form an incorporated formulation or preparation, thereby improving unexpectedly the shelf life and light resistance of said α-unsaturated amine derivative or salt.

The acids employed in the present invention include inorganic and organic acids. Examples of the inorganic acids include perchloric acid, hydrochloric acid, sulfuric acid, nitric acid, phosphoric acid, etc. Examples of the organic acids include L-ascorbic acid, acetic acid, succinic acid, benzoic acid, aspartic acid, citric acid, glutamic acid, oxalic acid, trichloroacetic acid, lactic acid, dichloroacetic acid, fumaric acid, maleic acid, malic acid, malonic acid, benzenesulfonic acid, isopropyl acid phosphate, etc. Among them, preferred examples are strong acids [those wherein the dissociation constant thereof is more than approximately $1 \times 10^{-3}$ or the pK thereof is less than 3 (Iwanami Rikagaku Jiten, 3rd Edition, 1971, Iwanami Publishing Company, Japan)]. Even in such instances, any of inorganic and organic acids can be used but preferably inorganic ones are employed. Among them, preferred examples are listed hereinbelow. Such inorganic acids include perchloric acid, hydrochloric acid, sulfuric acid, nitric acid, phosphoric acid, etc. Such organic acids include aspartic acid, citric acid, glutamic acid, oxalic acid, dichloroacetic acid, trichloroacetic acid, fumaric acid, maleic acid, malonic acid, benzenesulfonic acid, isopropyl acid phosphate, etc. More preferred examples are phosphoric acid, hydrochloric acid, oxalic acid, citric acid, benzenesulfonic acid, isopropyl acid phosphate, etc. Still more preferred examples are phosphoric acid, citric acid, benzenesulfonic acid, isopropyl acid phosphate, etc. Specifically, phosphoric acid is most preferable.

The solid carriers employed in the present invention are those capable of incorporating the α-unsaturated amine derivatives [I], [II] or salts thereof. Such solid carriers include those capable of adsorbing at least $5.0 \times 10^{-2}$ mmol/g of the active substance from solution or suspension adjusted to pH≦5. Specifically solid carriers capable of adsorbing from $5.0 \times 10^{-2}$ to $400 \times 10^{-2}$ mmol/g of the active substance therefrom are employed. Preferred examples are those capable of adsorbing from $10.0 \times 10^{-2}$ to $200 \times 10^{-2}$ mmol/g of the active substance therefrom, more preferably from $10.0 \times 10^{-2}$ to $100 \times 10^{-2}$ mmol/g of the active substance therefrom.

Examples of such solid carriers include clay mineral capable of adsorption, zeolite, activated charcoal, β-cyclodextrin, etc. Examples of such clay minerals include montmorillonite-saponite groups having 2:1 crystal structure type form and sepiolite having double-chain crystal structure type form. Among them, preferred examples are montmorillonite-saponite groups having 2:1 crystal structure type form.

Examples of such montmorillonite-saponite clay minerals include montmorillonite, beidellite, nontronite, saponite, hectorite, sauconite, as well as those containing any of montmorillonite, beidellite, nontronite, saponite, hectorite, sauconite, and the like as a main constituent, such as fuller's earth, terra alba, bentonite, and activated fuller's earth. Fuller's earth is more preferred.

The solid carriers capable of adsorption are not limited to those exemplified above but may include any substance capable of incorporating the α-unsaturated amine derivative [I], [II] or its salt thereinto, or including (or surrounding) the guest to form a complex such as an inclusion complex, and a clathrate.

Since conventional clays and kaolin have merely insufficient adsorption capacity, they do not work for improvement of the stability. Therefore, they are not suitable for the solid carrier capable of adsorption in the present invention.

The solid carrier usually employed in the present invention is powdery in application. The particle size is within 100 μm or less in diameter. The usual range thereof is from 1 to 100 μm, preferably from 10 to 80 μm. More preferred rages are from 20 to 50 μm.

An amount of the solid carrier (a total amount when two or more solid carriers are employed) in the composition according to the present invention is suitably in the range of about 1 to 95 wt% per total of the final formulation. For example, an appropriate range is about 1 to 90 wt%, preferably about 1 to 30 wt% in the case of a dust, DL dust, granule, and microgranule F. It is about 5 to 95 wt%, preferably about 50 to 90 wt% in the case of a wettable powder, and wettable granule, etc. An amount of said solid carrier (a total amount when two or more solid carriers are employed) is in the range of about 10 weight parts or more per one weight part of the active ingredient, preferably about 10 to 50 weight parts, more preferably about 10 to 20 weight parts.

An amount of the acid (a total amount when two or more acids are employed) in the composition according to the present invention is suitably in the range of about 0.0001 to 10 wt% as a net acid per total of the final formulation. For example, an appropriate range is about 0.0005 to 5 wt%, preferably about 0.0005 to 3 wt% in the case of a dust, DL dust, granule, and microgranule F. It is about 0.5 to 10 wt%, preferably about 0.5 to 5 wt% in the case of a wettable powder, and wettable granule, etc. An amount of said acid (a total amount when two or more acids are employed) is in the range of about 0.05 to 0.5 weight parts per one weight part of the solid carrier, preferably about 0.1 to 0.3 weight parts.

The proportion of the α-unsaturated amine derivative or salt thereof in the composition according to the present invention is suitably about 0.1 to 90 wt% per total of the final formulation. For example, an appropriate range is about 0.1 to 10 wt% in the case of a dust, DL dust, granule, and microgranule F, about 5 to 90 wt% in the case of a wettable powder, and wettable granule, etc. An amount of said solid carrier (a total amount when two or more solid carriers are employed) is in the range of about 0.1 to 100 weight parts per one weight part of α-unsaturated amine derivative or salt thereof, preferably 0.5 to 50 weight parts.

The agrochemical composition according to the present invention can be prepared or formulated under pH adjustment according to conventional methods for preparing agrochemical concentrated dusts. According to one embodiment, the agrochemical compositions are prepared or formulated by incorporating the active substance into the solid carrier under a pH 5.5 or less condition. For example, such preparations comprise;

(1) preparing an aqueous solution (or suspension) of at least one of the active substances, adjusting pH thereof to 5.5 or less, and then mixing (or blending) the resultant product with the solid carrier, depending on necessity, in admixture with other agrochemical adjuvants to incorporate said active substance into said solid carrier;

(2) preparing an aqueous solution (or suspension) of at least one of the active substances, and a mixture of the acid with the solid carrier, depending on necessity, in admixture with other agrochemical adjuvants wherein an amount of the acid employed is sufficient to achieve pH 5.5 or less in the resultant composition when the aqueous solution (or suspension) is added, and then mixing said aqueous solution (or suspension) with said mixture to incorporate said active substance into said solid carrier;

(3) mixing (or blending) at least one of the active substances, the solid carrier, and the acid with at least one of other solid carriers wherein an amount of the acid employed is sufficient to achieve pH 5.5 or less in the resultant composition when water (or an aqueous solution or suspension) is added, and then mixing the resultant mixture with said water (or an aqueous solution or suspension) to incorporate said active substance into said solid carrier; or (4) mixing (or blending) at least one of the active substances, and the solid carrier with at least one of other solid carriers, and then mixing the resultant mixture with an aqueous solution (or suspension) containing the acid to incorporate said active substance into or with said solid carrier wherein an amount of the acid employed is sufficient to achieve pH 5.5 or less in the resultant composition when the aqueous solution (or suspension) is admixed with said mixture.

The mixing (or blending) or admixing can be carried out by a mixer such as a mortar and pestle or kneader. The mixing or admixing is not limited to but may include any of techniques for the preparation of agrochemical agents or formulations which are well known to those who are skilled in the art. As the case may be, moisture can be removed by drying after mixing and incorporation.

Thus, in accordance with the present invention and using the methods used herein, it is important to adjust the pH of the solution (or suspension) containing the active substance, etc. to 5.5 or less in advance upon incorporation of said active substance into or with said stabilizer. The pH thereof is usually adjusted to 0.01 to 5.5, preferably 0.01 to 4.0, more preferably 0.1 to 3.0. In a preferred embodiment, a solution (or suspension) adjusted to pH about 3.0 is employed.

For example, the pH can be controlled by adding several drops of phosphoric acid into about 500 ml of the aqueous solution (or suspension) in the case of the above-mentioned processes (1) and (4). However, the pH can be controlled without any limitation but by means of buffering solutions and the like. The pH can readily be controlled by adding several drops of phosphoric acid into the solid carrier in the case of the above-mentioned processes (2) and (3).

Solvents for the aqueous solution (or suspension) employed in the present invention include water alone as well as in combination with organic solvents miscible with water. Preferred systems for the present invention are those containing water alone in view of agrochemical agents or formulations.

The stabilized composition according to the present invention is substantially tolerant to plants as well as human beings and animals (including fish) at or after an application. Thus, the composition according to the present invention is safe (harmless) and stable.

The composition according to the present invention is in a solid form. The composition can be applied as a suitable agrochemical solid formulation or preparation such as a dust, DL (driftless) dust, granule, wettable powder, water-dispersible granule, seed treating agent, and microgranule F.

These compositions may be admixed or formulated, if necessary, with other agrochemically active ingredients, and/or agrochemically acceptable vehicles such as dispersing agents, spreaders, wetting agents, mucilages, anti-blocking agents, agglomerating agents, binding agents, antioxidants, desiccants, etc.

Conventional solid carriers (diluents/extenders) include preferably mineral powders such as clays (e.g. fine powdered clays, etc.), talcs (e.g. talcum powder, agalmatolite powder, etc.), silicas (e.g. diatomaceous earth, mica powder, etc.), vegetable powders (e.g. soybean meal, tobacco powder, wheat flour, sawdust, etc.), calcium carbonate, sulfur powder, urea powder, and the like. For this purpose any adjuvant may be employed as long as it is agrochemically acceptable. These solid carriers may be used individually or in a suitable mixed form of two or more ingredients in a suitable ratio.

Surface-active agents (surfactants) which may optionally be employed, depending on necessity, as said dispersing agent, spreader, wetting agent, or penetrating agent, include various soaps and nonionic or anionic surface-active agents such as polyoxyethylene alkyl aryl ethers [e.g. Noigen TM and E.A 142 TM, Dai-ichi Kogyo Seiyaku K.K.], sodium alkylnaphthalene sulfonates [e.g. Newcalgen BX-C TM, Takemoto Yushi K.K.], block copolymers of ethylene oxide and propylene oxide [e.g. Newpol PE-64 TM, Sanyo Kasei K.K.], polycarboxlate type surface-active agents [e.g. Toxanon GR-30 TM, Sanyo Kasei K.K.], dialkylsulfosuccinic acid ester sodium salts [e.g. Neocol SW-C TM, Dai-ichi Kogyo Seiyaku K.K.], polyoxyethylene distyrenated phenyl ether sulfate ammonium salts [e.g. Dixzol 60A TM, Dai-ichi Kogyo Seiyaku K.K.], sodium lignin sulfonates, and potassium lignin sulfonates.

The surface-active agents which can be employed as said dispersing agent, spreader, wetting agent, or penetrating agent include various nonionic and anionic surface-active agents. Preferred examples of such surface-active agents include (1) Nonionic Surface-Active Agents polyoxyethylene alkyl aryl ethers [e.g. Noigen TM and E.A 142 TM, Dai-ichi Kogyo Seiyaku K.K.],
block copolymers of ethylene oxide and propylene oxide [e.g. Newpol PE-64 TM, Sanyo Kasei K.K.], (2) Anionic Surface-Active Agents polycarboxlate type surface-active agents [e.g. Toxanon GR-30 TM, Sanyo Kasei K.K.],
dialkylsulfosuccinic acid ester sodium salts [e.g. Neocol SW-C TM, Dai-ichi Kogyo Seiyaku K.K.],
polyoxyethylene distyrenated phenyl ether sulfate ammonium salts [e.g. Dixzol 60A TM, and Dixzol WK TM, Dai-ichi Kogyo Seiyaku K.K.],
sodium alkylnaphthalene sulfonates [e.g. Newcalgen BX-C TM, Takemoto Yushi K.K.],
sodium lignin sulfonates,
potassium lignin sulfonates, and the like.

A usual amount of the surface-active agents which may be employed in the composition is suitably in the range of about 0 to 30 wt% per total of the final formulation. For example, an appropriate range is preferably about 0 to 20 wt%.

Flowing aids include PAP-agents such as isopropyl acid phosphate, talcum, etc. Such flowing aids are optionally employed in the composition according to the present invention.

A usual amount of the flowing aids is suitably in the range of about 0 to 20 wt% per total of the final formulation. For example, an appropriate range is preferably about 0 to 10 wt%.

Anti-blocking agents include white carbon, diatomaceous earth, magnesium stearate, aluminum oxide, titanium dioxide, etc. Such anti-blocking agents are optionally employed in the composition according to the present invention.

A usual amount of the anti-blocking agents is suitably in the range of about 0 to 50 wt% per total of the final formulation. For example, an appropriate range is preferably about 0 to 20 wt%.

Agglomerating agents include liquid paraffin, ethylene glycol, diethylene glycol, triethylene glycol, polyisobutylene (e.g. IP Solvent-2835 TM, Idemitsu Sekiyu Kagaku K.K.), etc. Such agglomerating agents are optionally employed in the composition according to the present invention.

A usual amount of the agglomerating agents is suitably in the range of about 0 to 20 wt% per total of the final formulation. For example, an appropriate range is preferably about 0.2 to 10 wt%.

Binding agents include carboxymethylcellulose sodium salt, dextrin, α-starch, polyvinyl alcohol, sodium lignin sulfonate, potassium lignin sulfonate, etc. Such binding agents are optionally employed in the composition according to the present invention.

A usual amount of the binding agents is suitably in the range of about 0 to 30 wt% per total of the final formulation. For example, an appropriate range is preferably about 0.2 to 10 wt%.

Antioxidants include dibutylhydroxytoluene, 4,4-thiobis-6-tert-butyl-3-methylphenol, butylhydroxyanisole, paraoctylphenol, mono-, di- or tri- (a-methylbenzyl)-phenol, 2,6-di-tert-butyl-4-methylphenol, pentaerythritol tetrakis[3-(3,5-di-tert-butyl-4-hydroxyphenyl)]-propionate, etc. Such antioxidants are optionally employed in the composition according to the present invention.

A usual amount of the antioxidants is suitably in the range of about 0 to 30 wt% per total volume of the final formulation. For example, an appropriate range is preferably about 0 to 10 wt%.

Desiccants include anhydrous gypsum, silica gel powder, etc. Such desiccants are optionally employed in the composition according to the present invention.

A usual amount of the desiccants is suitably in the range of about 0 to 30 wt% per total of the final formulation. For example, an appropriate range is preferably about 0.5 to 20 wt%.

UV adsorbents include 2-(2'-hydroxy-5'-methylphenyl) benzotriazol, 2-ethoxy-2'-ethyloxalic acid bisanilide, succinic acid dimethyl-1-(2-hydroxyethyl)-4- hydroxy-2,2,6,6-tetramethylpireridine polymeric condensate, etc. Such UV adsorbents are optionally employed in the composition according to the present invention.

A usual amount of the UV adsorbents is suitably in the range of about 0 to 20 wt% per total of the final formulation. For example, an appropriate range is preferably about 0.5 to 10 wt%.

UV scattering agents include titanium dioxide, etc. Such UV scattering agents are optionally employed in the composition according to the present invention.

A usual amount of the UV scattering agents is suitably in the range of about 0 to 90 wt% per total of the final formulation. For example, an appropriate range is preferably about 1.0 to 20 wt%.

The composition containing the α-unsaturated amine derivative or salt thereof can be used, as the case may be, in combination with one or more species of agrochemically active substances such as fungicides (e.g. organosulfur fungicides, organophosphorus fungicides, organoarsenum fungicides, organochlorine fungicides, etc.), insecticides (e.g. organophosphorus insecticides, organochlorine insecticides, carbamate insecticides, pyrethroid insecticides, etc.), various antibiotics.

Representative examples of said agrochemically active substances include (the parentheses after the chemical names represent common names or abbreviations; they are hereinafter often quoted);

Carbamate Insecticides 2-isopropoxyphenyl N-methylcarbamate (PHC, propoxur),
o-cumenyl N-methylcarbamate (MIPC, isoprocarb),
o-sec-butyl N-methylcarbamate (BPMC, fenobucarb),
3,4-xylyl N-methylcarbamate (MPMC, xylylcarb),
m-tolyl N-methylcarbamate (MTMC, metolcarb),
3,5-xylyl N-methylcarbamate (XMC),
2-(ethylthiomethyl)phenyl N-methylcarbamate (ethiofencarb),
1-naphthyl N-methylcarbamate (NAC, carbaryl),
primicarb,
bendiocarb,
carbofuran,
furathiocarb,
carbosulfan,
benfuracarb,
methomyl, etc.;

Pyrethroid Insecticides cyfluthrin,
permethrin,
cypermethrin,
cyhalothrin,
fenpropathrin,
fenvalerate,
(RS) α-cyano-3-phenoxybenzyl (S)-2-(4-difluoromethoxyphenyl)-3-methylbutylate (flucythrinate),
flvalinate,
2-(4-ethoxyphenyl)-2-methylpropyl 3-phenoxybenzyl ether (ethofenprox),
cycloprothrin,
resmethrin,
allethrin,
pyrethrin, etc.;

Organophosphorus Insecticides

MPP (fenthion),
O,O-dimethyl O-(4-nitro-m-tolyl)thiophosphate (MEP, fenitrothion),
propaphos,
dimethyl p-cyanophenyl thiophosphate (CYAP, cyanophos),
prothiofos,
sulprofos,
profenofos,
EPN,
cyanofenphos,
acephate,
EPS (oxydeprofos),
disulfoton,
thiometon,
PAP (phenthoate),
S-1,2-bis(ethoxycarbonyl)ethyl dimethyl dithiophosphate (malathion),
dimethoate,
vamidothion,
(RS)-[0-1-(4-chloro)pyrazol-4-yl]0-ethyl S-propyl thiophosphate (pyraclofos),
DEP (trichlorfon),
BRP (naled),
DDVP (dichlorvos),
CVP (chlorfenvinphos),
CVMP (tetrachlorvinphos),
monocrotophos,
phosalone,
chlorpyrifos-methyl,
chlorpyrifos,
pirimiphosmethyl,
diazinon,
etrimfos,
pyridaphenthion,
quinalphos,
isoxathion,
DMTP (methidathion),
dioxabenzofos, etc.;

Organochlorine Insecticides 6,7,8,9,10,10-hexachloro-1,5,5a,6,9,9a-hexahydro-6,9-methano-2,4,3-benzodioxathiepin 3-oxide (endosulfan), etc.;

Other Insecticides

S,S'-[2-(dimethylamino)trimethylene]bis(thiocarbamate) (cartap),
5-dimethylamino-1,2,3-trithian oxalate (thiocyclam),
S,S'-[2-(dimethylamino)trimethylene]bis(benzenethiosulfonate) (bensultap),
2-tert-butylimino-3-isopropyl-5-phenyl-3,4,5,6-tetrahydro-2H-1,3,5-thiadiazin-4-one (buprofezin),
flufenoxuron,
diflubenzuron,
chlorfluazuron, etc.;

N-Heterocyclic Ergosterol Inhibitor Fungicides triflumizole,
triforine, etc.;

Carboxamide Fungicides mepronil,
flutolanil,
pencycuron,
oxycarboxin, etc.;

Dicarboximide Fungicides iprodione, vinclozolin,
procymidone, etc.;

Benzimidazole Fungicides benomyl, etc.;

Polyhaloalkylthio Fungicides captan, etc.;

Organophosphorus Fungicides

O-ethyl S,S-diphenyl dithiophosphate (EDDP, edifenphos),
O,O-diisopropyl S-benzyl thiophosphate (IBP, iprobenfos), etc.;

Organochlorine Fungicides 4,5,6,7-tetrachlorophthalide (fthalide),
tetrachloroisophthalonitrile (TPN, chlorothalonil),
pentachlorophenol (PCP), etc.;

Organosulfur Fungicides zinc ethylenebis(dithiocarbamate) (zineb),
manganese ethylenebis(dithiocarbamate) (maneb), etc.;

Organoarsenum Fungicides iron methanearsonate (MAF),
iron ammonium methanearsonate (MAFA), etc.;

Other Fungicides diclomezine,
5-methyl-1,2,4-triazolo[3,4-b]benzothiazole (tricyclazole),
pyroquilon,
isoprothiolane,
3-allyloxy-1,2-benzoisothiazole 1,1-dioxide (probenazole),
anilazine,
oxolinic acid,
dimethirimol,
(Z)-2'-methylacetophenone 4,6-dimethylpyrimidine-2-ylhydrazone
(ferimzon), etc.;

Antibiotics validamycin A,
kasugamycin,
mildiomycin,
blasticidin S,
polyoxin,
oxytetracycline, etc.

Preferred examples of such active ingredients are validamycin A, cartap, bensultap, probenazole, IBP, tricyclazole, ferimzon, ethofenprox, flucythrinate, fthalide, MEP, MTMC, BPMC, etc. More preferred examples of such active ingredients are validamycin A, cartap, bensultap, MEP, ferimzon, fthalide, etc.

Concrete examples of the mixed compositions according to the present invention include α-unsaturated amine derivatives [I], [II] or salt thereof.validamycin A, α-unsaturated amine derivatives [I], [II] or salt thereof.-cartap, α-unsaturated amine derivatives [I], [II] or salt thereof.bensultap, α-unsaturated amines [I], [II] or salt thereof.ferimzon.fthalide, etc.

The proportion of the agrochemically active substances excluding the α-unsaturated amine derivative [I], [II] or its salt in the mixed compositions according to the present invention is of the same value as mentioned above. Thus, it is suitably about 0.01 to 90 wt % per total of the final formulation. A total amount of the active substances in the mixed composition is in the range of about 0.01 to 90 wt %, preferably about 0.05 to 20 wt %, more preferably about 0.5 to 15 wt % per total of the final formulation.

Agrochemically active substances which are liquid at ambient temperature or melt near ambient temperature (e.g. ethofenprox, etc.) may be dissolved or dispersed in solvents such as high boiling point solvents (e.g. phenylxylylethane, di-2-ethylhexyladipate, 2-ethylhexylphenylphosphate, etc.) before use.

According to the present invention, the composition can be employed in combination with acaricides, miticides, nematocides, herbicides, plant hormones, plant growth regulators, synergists, attractants, repellents, pigments, fertilizers, manures, or the like.

In the case where the pesticide of the present invention is in the form of a wettable powder, it may be employed by diluting, for example, about 30 to 4000 times, preferably 300 to 3000 times, with water before use. A final concentration of active ingredient is ususally in the range of 5 to 1,000 ppm. A preferred final concentration of the α-unsaturated amine derivative or its salt is in the range of 10 to 300 ppm.

The application amount can vary over a wide range, depending on the season, place and method of application, etc. Preferably, the pesticide of the invention is employed, in general, in such a manner that the proportion of the active ingredient (i.e. α-unsaturated amine and/or salt thereof) is in the range of 10 to 500 g, more preferably 50 to 300 g, per ten acre.

The compositions according to the present invention are applied to target pests, for example, by being sprinkled directly over leaves or stems of plants, by treating soils around roots, or in nursery boxes.

The compositions can be effective in controlling or eradicating horticultural insect pests and plant parasitic insects, for example, on rice, vegetables (e.g. cabbage, Japanese cabbage (*Brassica rapa* L. var. *amplexicaulis* T$_{NAKA}$ et O$_{NO}$), Japanese radish (*Raphanus sativus* L. var. *hortensis* B$_{ACKER}$), cucumber, potato, etc.), fruit trees (e.g. citrus, pear, etc.), tea, tobacco, and the like. Such pests include Lepidoptera pests such as, for example, *Chilo suppressalis, Cnaphalocrocis medinalis, Pseudaletia separata, Mamestra brassicae, Plutella xylostella, Caloptilia theivora,* Adoxophyes sp.; Coleoptera pests such as, for example, *Lissorhoptrus oryzophilus, Echinocnemus squameus, Oulema oryzae, Aulacophora femoralis;* Hemiptera pests such as, for example, *Nephotettix cincticeps, Nilaparvata lugens, Laodelphax striatellus, Sogatella furcifera, Trialeurodes vaporariorum, Bemisia tabaci, Psylla pyricola;* Aphids such as, for example, *Aphis gossypii, Myzus persicae, Macrosiphum euphorbiae;* Thysanoptera pests such as, for example, *Scirtothrips dorsalis, Thrips palmi;* etc.

Examples of these pests include Asiatic rice borer (rice stem borer, striped rice borer), rice leafroller (rice leaffolder), armyworm (rice armyworm, rice ear-cutting caterpillar), cabbage armyworm, diamondback (cabbage moth), tea leafroller, tea tortorix, rice water weevil, rice curculio (rice plant weevil), rice leaf beetle, cucurbit leaf beetle, green rice leafhopper, whitebacked rice planthopper, brown rice planthopper, small brown planthopper, greenhouse whitefly (glasshouse whitefly), sweetpotato whitefly, pear psylla, cotton aphid (melon aphid), green peach aphid, peach-potato aphid, potato aphid (tomato aphid), yellow tea thrips, chillie thrips, etc.

The compositions can be applied to insect habitats (for example, breeding or swarming areas) in a permanently preventive (i.e. before infestation) or eradicative manner (i.e. after infestation).

The compositions of the present invention can be prepared according to the methods described herein or in the working examples.

Preferred compositions according to the present invention are DL dusts, granules, and wettable powders.

A preferred composition of DL dusts contains:
active substance (α-unsaturated amine [I] and/or salt thereof, etc.)
solid carrier (fuller's earth, etc.)
acid (phosphoric acid, etc.)
fixing agent (anionic surface-active agent [Neocol SW-C TM, etc.], etc.) and
DL agent (IP Solvent TM, etc.).

A preferred composition of granules contains:
active substance (α-unsaturated amine [I] and/or salt thereof, etc.)
solid carrier (fuller's earth, etc.)
acid (phosphoric acid, etc.)
binding agent (dextrin, etc.)
penetrating agent (anionic surface-active agent [Toxanon GR-30 TM, etc.], etc.) and
bulking agent (clay, etc.).

A preferred composition of wettable powders contains:
active substance (α-unsaturated amine [I] and/or salt thereof, etc.)
solid carrier (fuller's earth, etc.)
acid (phosphoric acid, etc.) and
dispersing agent (anionic surface-active agent [Dixzol WK TM, etc.], etc.).

A more preferred composition of DL dusts contains:
active substance (α-unsaturated amine [II] and/or salt thereof, etc.)
solid carrier (fuller's earth, etc.)
acid (phosphoric acid, etc.)
fixing agent (anionic surface-active agent [Neocol SW-C TM, etc.], etc.) and
DL agent (IP Solvent TM, etc.).

A more preferred composition of granules contains:
active substance (α-unsaturated amine [II] and/or salt thereof, etc.)
solid carrier (fuller's earth, etc.)
acid (phosphoric acid, etc.)
binding agent (dextrin, etc.)
penetrating agent (anionic surface-active agent [Toxanon GR-30 TM, etc.], etc.) and
bulking agent (clay, etc.).

A more preferred composition of wettable powders contains:
active substance (α-unsaturated amine [II] and/or salt thereof, etc.)
solid carrier (fuller's earth, etc.)
acid (phosphoric acid, etc.) and
dispersing agent (anionic surface-active agent [Dixzol WK TM, etc.], etc.).

The compositions according to the present invention can inhibit the degradation of the α-unsaturated amine derivative [I], [II] or its salt even when they are stored for long time and prevent the photodegradation by sunlight even when they are sprinkled on paddy and upland fields, thereby being stable, exerting essentially no adverse effect on plants and advantageously useful in controlling, combatting or preventing plant pests or harmful organisms.

Further, the compositions according to the present invention can include other agrochemical active substances which could not be admixed with the α-unsaturated amine derivatives [I], [II] or salts thereof in the prior art formulations.

Still, the compositions according to the present invention have an excellent availability of the active ingredient after application. Advantageously, the compositions according to the present invention can be readily manufactured by industrial processes.

The pesticidal composition thus obtained is extremely low in toxicity and is stable, safe and excellent as an agrochemical. It can be used in the same manner as in conventional insecticides and exert superior stability in comparison with conventional products.

The foregoing is merely illustrative of the invention and is not intended to limit the invention to the disclosed compounds and compositions.

EXAMPLES

By the following reference examples, working examples, and test examples, the present invention will be explained more concretely, but they should not be interpreted as limiting the invention in any manner.

REFERENCE EXAMPLE 1

DL Type Dust (no solid carrier capable of adsorption, and without pH adjustment)

To 98.25 parts of fine powdered clay was added 0.25 parts of Compound No. 3, followed by 1.0 parts of liquid parafin (Driless C TM, hereinafter "Driless C TM") and 0.5 parts of white carbon, and the resulting mixture was well mixed by an automated mortar. The mixture was then triturated by Bantam mill to afford DL type dusts containing Compound No. 3.

REFERENCE EXAMPLE 2

DL Type Dust (no solid carrier capable of adsorption, and without pH adjustment; admixture with cartap)

To 96.25 parts of fine powdered clay was added 0.25 parts of Compound No. 3, followed by 2.0 parts of cartap, 1.0 parts of Driless C TM and 0.5 parts of white carbon, and the resulting mixture was well mixed by an automated mortar. The mixture was then triturated by Bantam mill to afford DL type dusts containing the mixture of Compound No. 3 and cartap.

REFERENCE EXAMPLE 3

DL Type Dust (no solid carrier capable of adsorption, and without pH adjustment; admixture with validamycin A)

To 97.95 parts of fine powdered clay was added 0.25 parts of Compound No. 3, followed by 0.3 parts of validamycin A, 1.0 parts of Driless C TM and 0.5 parts of white carbon, and the resulting mixture was well mixed by an automated mortar. The mixture was then triturated by Bantam mill to afford DL type dusts containing the mixture of Compound No. 3 and validamycin A.

REFERENCE EXAMPLE 4

DL Type Dust (no solid carrier capable of adsorption, and without pH adjustment; admixture with ferimzon and fthalide)

To 94.75 parts of fine powdered clay was added 0.25 parts of Compound No. 3, followed by 2.0 parts of ferimzon, 1.5 parts of fthalide, 1.0 parts of Driless C TM and 0.5 parts of white carbon, and the resulting mixture was well mixed by an automated mortar. The mixture was then triturated by Bantam mill to afford DL type dusts containing the mixture of Compound No. 3, ferimzon, and fthalide.

REFERENCE EXAMPLE 5

Granule (no solid carrier capable of adsorption)

To 93.0 parts of fine powdered clay was added 1.0 parts of Compound No. 3, followed by 5.0 parts of dextrin and 1.0 parts of 85% phosphoric acid, and the resulting mixture was well mixed. To the mixture was added water and the wet mixture was well kneaded. The damp mass was granulated through an oscillating granulator (screen size: 1.0 mm in diameter) to form wet products. The products was dried and sieved to granules ranging from 10-mesh to 32-mesh.

REFERENCE EXAMPLE 6

Wettable Powder (no solid carrier capable of adsorption, and without pH adjustment)

To 82.0 parts of clay for a wettable powder was added 10.0 parts of Compound No. 3, followed by 5.0 parts of Newcalgen BX-C TM (Takemoto Yushi K.K., Japan) and 3.0 parts of white carbon, and the resulting mixture was well blended by an automated mortar. The mixture was pulverized by a fine grinding mill to afford wettable powders containing the mixture of Compound No. 3.

REFERENCE EXAMPLE 7

DL Type Dust (no solid carrier capable of adsorption, and without pH adjustment)

Compound No. 3 (20.0 parts) was dissolved in 80.0 parts of water (adjusted to pH 3). The solution (1.25 parts) was blended well with 5.0 parts of fine powdered clay. To 6.25 parts of the resulting mixture was added 7.25 parts of fine powdered clay, followed by 1.0 parts of Driless C TM, 0.5 parts of white carbon and 15.0 parts of anhydrous gypsum and the mixture was well blended by an automated mortar. The mixture was then triturated by Bantam mill to afford DL type dusts containing Compound No. 3.

REFERENCE EXAMPLE 8

DL Type Dust

To 93.25 parts of fine powdered clay was added 0.25 parts of Compound No. 3, followed by 1.0 parts of Driless TM, 5.0 parts of fuller's earth and 0.5 parts of white carbon, and the resulting mixture was well mixed by an automated mortar. The mixture was then triturated by Bantam mill to afford DL type dusts containing Compound No. 3.

EXAMPLE 1

DL Type Dust (Process ①)

Compound No. 3 (20.0 parts) was dissolved in 80.0 parts of water (previously adjusted with phosphoric acid to pH 3 by measuring with a pH meter). The solution (1.25 parts) was blended well with 5.0 parts of fuller's earth to become homogeneous. To 6.25 parts of the resulting mixture was added 77.25 parts of fine powdered clay, followed by 1.0 parts of Driless C TM, 0.5 parts of white carbon and 15.0 parts of anhydrous gypsum and the mixture was well blended by an automated mortar. The mixture was then triturated by Bantam mill to afford DL type dusts containing Compound No. 3.

EXAMPLE 2

DL Type Dust (Process ①)

Compound No. 3 (20.0 parts) was dissolved in 80.0 parts of water (previously adjusted with phosphoric acid to pH 3 by measuring with a pH meter). The solution (1.25 parts) was blended well with 5.0 parts of fuller's earth, 77.25 parts of fine powdered clay, 1.0 parts of Driless C TM, 0.5 parts of white carbon and 15.0 parts of anhydrous gypsum, and the resulting mixture was well blended by an automated mortar. The mixture was then triturated by Bantam mill to afford DL type dusts containing Compound No. 3.

EXAMPLE 3

DL Type Dust (Process ①)

Compound No. 3 (20.0 parts) was dissolved in 80.0 parts of water (previously adjusted with phosphoric acid to pH 3 by measuring with a pH meter). The solution (1.25 parts) was blended well with 5.0 parts of sepiolite (Aidplus TM, Takeda Chemical Industries, Ltd) to become homogeneous. To 6.25 parts of the resulting mixture was added 77.25 parts of fine powdered clay, followed by 1.0 parts of Driless C TM, 0.5 parts of white carbon and 15.0 parts of anhydrous gypsum, and the resulting mixture was well blended by an automated mortar. The mixture was then triturated by Bantam mill to afford DL type dusts containing Compound No. 3.

EXAMPLE 4

DL Type Dust (Process ①)

Compound No. 3 (20.0 parts) was dissolved in 80.0 parts of water (previously adjusted with phosphoric acid to pH 3 by measuring with a pH meter). The solution (1.25 parts) was blended well with 5.0 parts of β-cyclodextrin to become homogeneous. To 6.25 parts of the resulting mixture was added 77.25 parts of fine powdered clay, followed by 1.0 parts of Driless C TM, 0.5 parts of white carbon and 15.0 parts of anhydrous gypsum, and the resulting mixture was well blended by an automated mortar. The mixture was then triturated by Bantam mill to afford DL type dusts containing Compound No. 3.

EXAMPLE 5

DL Type Dust (Process ①)

Compound No. 3 (20.0 parts) was dissolved in 80.0 parts of water (previously adjusted with phosphoric acid to pH 3 by measuring with a pH meter). The solution (1.25 parts) was blended well with 5.0 parts of fuller's earth by an automated mortar to become homogeneous. To 6.25 parts of the resulting mixture was added 76.95 parts of fine powdered clay, followed by 0.3 parts of validamycin A, 1.0 parts of Driless C TM, 0.5 parts of white carbon and 15.0 parts of anhydrous gypsum, and the resulting mixture was well blended by an automated mortar. The mixture was then triturated by Bantam mill to afford DL type dusts containing the mixture of Compound No. 3 and validamycin A.

EXAMPLE 6

DL Type Dust (Process ①)

Compound No. 3 (20.0 parts) was dissolved in 80.0 parts of water (previously adjusted with phosphoric acid to pH 3 by measuring with a pH meter). The solution (1.25 parts) was blended well with 5.0 parts of fuller's earth by an automated mortar to become homogeneous. To 6.25 parts of the resulting mixture was added 75.25 parts of fine powdered clay, followed by 2.0 parts of cartap, 1.0 parts of Driless C TM, 0.5 parts of white carbon and 15.0 parts of anhydrous gypsum, and the resulting mixture was well blended by an automated mortar. The mixture was then triturated by Bantam mill to afford DL type dusts containing the mixture of Compound No. 3 and cartap.

EXAMPLE 7

DL Type Dust (Process ①)

Compound No. 3 (15.0 parts) was mixed and dissolved with 55.0 parts of water and 30.0 parts of phosphoric acid. The solution (1.75 parts) was blended well with 5.0 parts of fuller's earth by an automated mortar to become homogeneous. To 6.75 parts of the resulting mixture was added 76.75 parts of fine powdered clay, followed by 1.0 parts of IP Solvent TM, 0.5 parts of white carbon and 15.0 parts of anhydrous gypsum, and the resulting mixture was well blended by an automated mortar. The mixture was then triturated by Bantam mill to afford DL type dusts containing Compound No. 3. The 10% suspension of the DL type dust was measured by a pH meter to exhibit pH 4.5.

EXAMPLE 8

DL Type Dust (Process ②)

Compound No.3 (20.0 parts) was dissolved in 80.0 parts of water. The aqueous solution (1.25 parts) was added to a mixture of phosphoric acid (0.5 parts) and fuller's earth (5.0 parts) (previously blended well). The resulting mixture was well blended by an automated mortar to become homogeneous. Then the mixture was dried at 60° C. in vacuo. To 5.75 parts of the dried mixture was added 77.75 parts of fine powdered clay, followed by 1.0 parts of IP Solvent TM, 0.5 parts of white carbon and 15.0 parts of anhydrous gypsum, and the resulting mixture was well blended by an automated mortar. The mixture was then triturated by Bantam mill to afford DL type dusts containing Compound No.3. The 10% suspension of the DL type dust was measured by a pH meter to exhibit pH 4.5.

EXAMPLE 9

DL Type Dust (Process ①)

Compound No.3 (2.0 parts) was dissolved in 58.0 parts of water (previously adjusted with phosphoric acid to pH 3 by measuring with a pH meter). The solution (60.0 parts) was blended well with 40.0 parts of fuller's earth to become homogeneous and the resulting mixture was dried by a spray-dryer (L-8 Type, Ohokawara Kakouki K. K., Japan). To 5.5 parts of the dried mixture was added 91.5 parts of fine powdered clay, followed by 0.5 parts of IP Solvent TM, 0.5 parts of ultra-pure, microparticle aluminum oxide and 2.0 parts of Neocol SW-C TM, and the resulting mixture was well blended by an automated mortar. The mixture was then triturated by Bantam mill to afford DL type dusts containing Compound No.3.

EXAMPLE 10

DL Type Dust (Process ①)

Compound No.1 (20.0 parts) was dissolved in 80.0 parts of water (previously adjusted with phosphoric acid to pH 3 by measuring with a pH meter). The solution (1.25 parts) was blended well with 5.0 parts of fuller's earth by an automated mortar to become homogeneous. To 6.25 parts of the resulting mixture was added 77.25 parts of fine powdered clay, followed by 1.0 parts of IP Solvent TM, 0.5 parts of white carbon and 15.0 parts of anhydrous gypsum, and the resulting mixture was well blended by an automated mortar. The mixture was then triturated by Bantam mill to afford DL type dusts containing Compound No.1.

EXAMPLE 11

DL Type Dust (Process ①)

Compound No.1 (20.0 parts) was dissolved in 80.0 parts of water (previously adjusted with phosphoric acid to pH 3 by measuring with a pH meter). To 1.25 parts of the solution was added 5.0 parts of fuller's earth, followed by 77.25 parts of fine powdered clay, 1.0 parts of Driless C TM, 0.5 parts of white carbon and 15.0 parts of anhydrous gypsum, and the resulting mixture was well blended by an automated mortar. The mixture was then triturated by Bantam mill to afford DL type dusts containing Compound No.1.

EXAMPLE 12

DL Type Dust (Process ①)

Compound No.1 (15.0 parts) was mixed and dissolved with 55.0 parts of water and 30.0 parts of phosphoric acid. The solution (1.75 parts) was blended well with 5.0 parts of fuller's earth by an automated mortar to become homogeneous. To 6.25 parts of the resulting mixture was added 77.25 parts of fine powdered clay, followed by 1.0 parts of IP Solvent TM, 0.5 parts of white carbon and 15.0 parts of anhydrous gypsum, and the resulting mixture was well blended by an automated mortar. The mixture was then triturated by Bantam mill to afford DL type dusts containing Compound No.1. The 10% suspension of the DL type dust was measured by a pH meter to exhibit pH 4.3.

EXAMPLE 13

DL Type Dust (Process ②)

Compound No.1 (20.0 parts) was dissolved in 80.0 parts of water. The aqueous solution (1.25 parts) was added to a mixture of phosphoric acid (0.5 parts) and fuller's earth (5.0 parts) (previously blended well). The resulting mixture was well blended by an automated mortar to become homogeneous. Then the mixture was dried at 60° C. in vacuo. To 5.75 parts of the dried mixture was added 77.75 parts of fine powdered clay, followed by 1.0 parts of IP Solvent TM, 0.5 parts of white carbon and 15.0 parts of anhydrous gypsum, and the resulting mixture was well blended by an automated mortar. The mixture was then triturated by Bantam mill to afford DL type dusts containing Compound No.1. The 10% suspension of the DL type dust was measured by a pH meter to exhibit pH 4.4.

EXAMPLE 14

Granule (Process ③)

To 83.0 parts of fine powdered clay was added 10.0 parts of fuller's earth, followed by 1.0 parts of Compound No.3, 5.0 parts of dextrin and 1.0 parts of 85% phosphoric acid, and the resulting mixture was well mixed. To the mixture was added water and the wet mixture was well kneaded. The damp mass was granulated through an oscillating granulator (screen size: 1.0 mm in diameter) to form wet products. The products was dried and sieved to granules ranging from 10-mesh to 32-mesh. After pulverization of the granules, the 10% suspension thereof was measured by a pH meter to exhibit pH 3.1.

EXAMPLE 15

Granule (Process ④)

To 83.0 parts of fine powdered clay was added 10.0 parts of fuller's earth, followed by 1.0 parts of Compound No.3, 5.0 parts of dextrin, and the resulting mixture was well mixed. To the mixture was added an aqueous solution containing 1.0 parts of 85% phosphoric acid and the wet mixture was well kneaded. The damp mass was granulated through an oscillating granulator (screen size: 1.0 mm in diameter) to form wet products. The products was dried and sieved to granules ranging from 10-mesh to 32-mesh. After pulverization of the granules, the 10% suspension thereof was measured by a pH meter to exhibit pH 3.0.

EXAMPLE 16

Wettable Powder (Process ④)

To 77.0 parts of fuller's earth was added 10.0 parts of Compound No.3, followed by 5.0 parts of 85% phosphoric acid, 5.0 parts of Newcalgen BX-C ™ (Takemoto Yushi K. K., Japan) and 3.0 parts of white carbon, and the resulting mixture was well blended by an automated mortar. The mixture was pulverized by a fine grinding mill to afford wettable powders.

EXPERIMENTAL EXAMPLE 1

Shelf Life Stability Test

Each mixed formulation obtained in Examples 1 to 16 and Reference Examples 1 to 8 (each 20 g) was stored at a determined temperature for a determined time in a paper pack for powdery dusts, paper pack for granules, or aluminum pack for wettable powders. Then the sample was taken out of the pack. A determined amount of the sample (10 mg as α-unsaturated amine derivatives or salts thereof) was measured accurately, and extracted by shaking with 40 ml of acetonitrile: 0.5M aq. $KH_2PO_4$-50/50 (v/v) for 30 min.

A content of α-unsaturated amine derivatives or salts thereof in the extract was measured by high performance liquid chromatography (HPLC, column; Nucleosil 10-$C_{18}$, Gaschro, Industries, K. K., Japan; eluting solvent; acetonitrile: 0.5M aq. $KH_2PO_4$-50/50 (v/v)).

A degradation percent (%) of α-unsaturated amine derivatives or salts thereof was calculated according to the following formula:

Degradation of α-unsaturated amine derivatives or salts thereof (%) =

$$\left\{ 1 - \frac{\text{Residual } \alpha\text{-unsaturated amine derivatives or salts thereof in preparations after storage for determined term at determined temperature}}{\text{Content of } \alpha\text{-unsaturated amine derivatives or salts thereof in preparations imediately after manufacture}} \right\} \times 100$$

The results are shown in Tables 1 to 3.

TABLE 1

Shelf Life of α-Unsaturated Amine Derivatives or Salts Thereof in Single or Mixed DL Type Dusts

| Test Preparation | Stabilizer | Degradation of α-Unsaturated Amine Derivatives or Salts Thereof at 40° C. for 2 months |
|---|---|---|
| Example 1 | Fuller's earth | 1.5% |
| Example 2 | Fuller's earth | 1.7% |
| Example 3 | Sepiolite | 7.3% |
| Example 4 | β-Cyclodextrin | 3.3% |
| Example 5 | Fuller's earth | 1.6% |
| Example 6 | Fuller's earth | 1.7% |
| Example 7 | Fuller's earth | 1.2% |
| Example 8 | Fuller's earth | 3.2% |
| Control: | | |
| Reference Example 1 | None | 21.6% |
| Reference Example 7 | Fine powdered clay | 36.3% |
| Reference Example 8 | Fuller's earth (None of acid) | 17.8% |

TABLE 2

Shelf Life of α-Unsaturated Amine Derivatives or Salts Thereof in Granules

| Test Preparation | Stabilizer | Degradation of α-Unsaturated Amine Derivatives or Salts Thereof at 40° C. for 2 months |
|---|---|---|
| Example 14 | Fuller's earth | 4.1% |
| Control: | | |
| Reference Example 5 | None | 17.7% |

TABLE 3

Shelf Life of α-Unsaturated Amine Derivatives or Salts Thereof in Wettable Powders

| Test Preparation | Stabilizer | Degradation of α-Unsaturated Amine Derivatives or Salts Thereof at 40° C. for 2 months |
|---|---|---|
| Example 16 | Fuller's earth | 1.2% |
| Control: | | |
| Reference Example 6 | None | 10.3% |

EXPERIMENTAL EXAMPLE 2

Stability Test for Photolytic Degradation

The formulation obtained in Example 8 and Reference Example 6 (each 1 g) was diluted with 1,000 ml of water to form a 1,000-fold dilution. The dilution (5 ml) was put into a Petri dish (diameter: 8.6 cm×height: 2.0 cm) homogeneously, and then dried at 60° C. for 2 hours in vacuo. The duplicate samples were prepared, i.e. one for dark and the other for exposure to sunlight.

After the exposure to sunlight, the α-unsaturated amine derivative or its salt was extracted by shaking with 50 ml of acetonitrile: 0.5M aq. $KH_2PO_4$-50/50 (v/v).

A content of α-unsaturated amine derivatives or salts thereof in the extract was measured by high performance liquid chromatography (HPLC, column; Nucleosil 10-$C_{18}$, Gaschro, Industries, K. K.; eluting solvent; acetonitrile: 0.5M aq. $KH_2PO_4$-50/50 (v/v)).

TABLE 4

Resistance against Photodegradation of α-Unsaturated Amine Derivatives or Salts Thereof after Sprinkling Wettable Powders

| Test Preparation | | Recovery of α-Unsaturated Amine Derivatives or Salts Thereof at 40° C. for 2 months | Residual Ratio |
|---|---|---|---|
| Example 16 | (Dark) | 96.1% | 100.0% |
| Example 16 | (Sunlight) | 79.6% | 88.3% |
| Control: | | | |
| Reference Example 6 | (Dark) | 97.5% | 100.0% |
| Reference Example 6 | (Sunlight) | 33.5% | 34.3% |

Recovery: Recover ratio of α-unsaturated amine derivatives or salts thereof to added amounts
Residual Ratio: Determined value of residual α-unsaturated amine derivatives or salts thereof in preparations exosed to the sunlight versus those in the dark (= 100).

EXPERIMENTAL EXAMPLE 3

Adsorption Test

Five hundred milligrams of Compound 3 was measured accurately, put into a 100 ml glass cylindrical graduate, and dissolved in purified water (adjusted previously to pH 3 or 6) to form a determined volume.

Five hundred milligrams of fuller's earth was measured accurately, and put into a 100 ml Erlenmeyer flask. To the Erlenmeyer flask was added said solution by means of a 40 ml volumetric pipette. The resulting suspension was shaken at 26° C. for 3 hours.

After removal of the fuller's earth by centrifugation at 3000 rpm, the concentration of Compound 3 in the supernatant was measured by high performance liquid chromatography (HPLC, column; Nucleosil 10-$C_{18}$, Gaschro, Industries, K. K.; eluting solvent; acetonitrile: 0.5M aq. $KH_2PO_4$-50/50 (v/v)). An amount of Compound 3 incorporated into the fuller's earth was estimated from the observation.

TABLE 5

Adsorption of α-Unsaturated Amine Derivatives or Salts Thereof on Fuller's Earth

| pH | Adsorption Amount of α-Unsaturated Amine Derivatives Salts Thereof on Fuller's earth (mmol/g) |
|---|---|
| 3 | 42.6 × $10^{-2}$ |
| 6 | 10.9 × $10^{-2}$ |

The adsorption amount was calculated according to the following formula:

Adsorption=(Compound 3 in the Aqueous Solution−Compound 3 in the Supernatant)/fuller's earth Added

EXPERIMENTAL EXAMPLE 4

Adsorption Test

An amount of the adsorbed compound on the fine powdered clay at pH 3,0 was measured in the same manner as in Experimental Example 3.

TABLE 6

Adsorption of α-Unsaturated Amine Derivatives or Salts Thereof on Fine Powdered Clay

| pH | Adsorption Amount of α-Unsaturated Amine Derivatives Salts Thereof on Fine Powdered Clay (mmol/g) |
|---|---|
| 3 | 3.1 × $10^{-2}$ |

What is claimed is:

1. An agrochemical composition which comprises:
(i) at least one α-unsaturated amine derivative having the following formula:

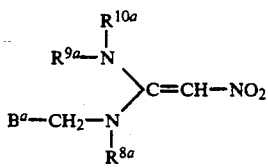

wherein $B^a$ is a substituted or unsubstituted pyridyl or thiazolyl group, and $R^{8a}$, $R^{9a}$ and $R^{10a}$ are each independently hydrogen; an alkyl, alkenyl, alkynyl, cycloalkyl, acyl, or alkoxycarbonyl group, or an agrochemically acceptable salt thereof;
(ii) an acid whose dissociation constant is at least about $1 \times 10^{-3}$; and
(iii) an agrochemically acceptable solid carrier which is capable of adsorbing at least $5.0 \times 10^{-2}$ mmol/g of the α-unsaturated amine derivative or salt thereof from a solution or suspension adjusted to a pH less than or equal to 5, both the α-unsaturated amine derivative and the acid each being incorporated into the agrochemically acceptable carrier.

2. The agrochemical composition according to claim 1, in which $B^a$ is a group having the formula:

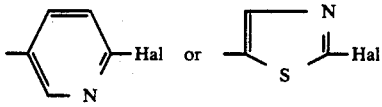

wherein Hal is halogen.

3. The agrochemical composition according to claim 1, comprising a compound of the formula:

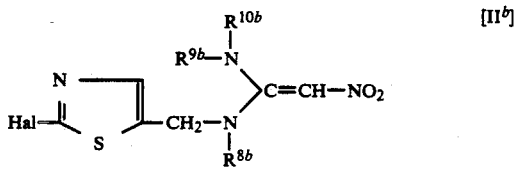

[II$^b$]

wherein $R^{8\,b}$, $R^{9\,b}$, and $R^{10\,b}$ are each independently hydrogen or an alkyl group, and Hal is halogen, or

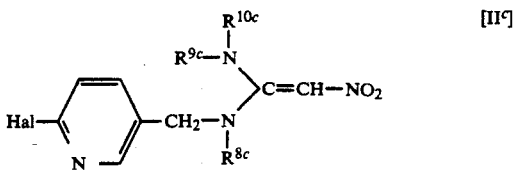

[II$^c$]

wherein $R^{8c}$, $R^{9c}$, and $R^{10c}$ are each independently hydrogen or an alkyl group, and Hal is halogen, or an agrochemically acceptable salt thereof.

4. The agrochemical composition according to claim 1, in which the α-unsaturated amine derivative is 1-[N-(6-chloro-3-pyridylmethyl)-N-ethyl]amino-1-methylamino-2-nitroethylene or an agrochemically acceptable salt thereof.

5. The agrochemical composition according to claim 1, in which the acid is selected from the group consisting of perchloric acid, hydrochloric acid, sulfuric acid, nitric acid, phosphoric acid, aspartic acid, citric acid, glutamic acid, oxalic acid, dichloroacetic acid, trichloroacetic acid, fumaric acid, maleic acid, malonic acid, benzenesulfonic acid, and isopropyl acid phosphate.

6. The agrochemical composition according to claim 1, in which the agrochemically acceptable solid carrier is selected from the group consisting of clay minerals capable of adsorption, zeolite, activated charcoal, and β-cyclodextrin.

7. The agrochemical composition according to claim 1, in which the solid carrier is selected from the group consisting of montmorillonite-saponite groups having 2:1 crystal structure type form and sepiolite having double-chain crystal structure type form.

8. The agrochemical composition according to claim 1, in which the agrochemically acceptable solid carrier is selected from the group consisting of montmorillonite, beidellite, nontronite, saponite, hectorite, sauconite, fuller's earth, terra alba, bentonite, and activated fuller's earth.

9. The agrochemical composition according to claim 1, in which the agrochemically acceptable solid carrier is fuller's earth.

10. The agrochemical composition according to claim 1, in which contains one or more species of agrochemically active substances in addition to at least one of the α-unsaturated amine derivatives.

* * * * *